(12) United States Patent
Mullins et al.

(10) Patent No.: US 8,914,555 B2
(45) Date of Patent: *Dec. 16, 2014

(54) METHODS, SYSTEMS AND APPARATUS FOR DETERMINING WHETHER AN ACCESSORY INCLUDES PARTICULAR CIRCUITRY

(71) Applicant: Apple Inc., Cupertino, CA (US)

(72) Inventors: Scott Mullins, Morgan Hill, CA (US); Alexei Kosut, Mountain View, CA (US); Jeffrey J. Terlizzi, San Francisco, CA (US); Zachary C. Rich, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/151,731

(22) Filed: Jan. 9, 2014

(65) Prior Publication Data
US 2014/0125312 A1 May 8, 2014

Related U.S. Application Data

(63) Continuation of application No. 13/607,473, filed on Sep. 7, 2012, now Pat. No. 8,683,090.

(60) Provisional application No. 61/635,652, filed on Apr. 19, 2012.

(51) Int. Cl.
| | | |
|---|---|---|
| G06F 3/00 | (2006.01) | |
| G01R 31/28 | (2006.01) | |
| G01N 27/00 | (2006.01) | |
| H02H 3/20 | (2006.01) | |
| G06F 1/26 | (2006.01) | |
| G01R 19/00 | (2006.01) | |
| H02H 9/02 | (2006.01) | |
| H02J 4/00 | (2006.01) | |
| H02J 7/00 | (2006.01) | |

(52) U.S. Cl.
CPC ............... *G01N 27/00* (2013.01); *G01R 31/28* (2013.01); *H02J 7/0042* (2013.01); *H02H 3/20* (2013.01); *G06F 1/266* (2013.01); *G01R 19/0084* (2013.01); *H02H 9/02* (2013.01); *H02J 4/00* (2013.01)
USPC ................ 710/16; 710/62; 320/114; 713/310

(58) Field of Classification Search
CPC ........................................................ G06F 3/00
USPC ............ 710/15–19, 62, 72; 320/114; 713/310
See application file for complete search history.

(56) References Cited

U.S. PATENT DOCUMENTS

| | | | | |
|---|---|---|---|---|
| 3,988,725 A | * | 10/1976 | Doherty | 340/510 |
| 5,568,037 A | | 10/1996 | Massaroni et al. | |

(Continued)

OTHER PUBLICATIONS

International Search Report and Written Opinion for PCT Application No. PCT/US2013/035443, mailed Jun. 11, 2013, 13 pages.

(Continued)

*Primary Examiner* — Christopher Shin
(74) *Attorney, Agent, or Firm* — Kilpatrick Townsend & Stockton LLP

(57) ABSTRACT

Methods, systems, and apparatus for determining whether an accessory includes particular circuitry. A host device may measure a first voltage and a second voltage received from an accessory, where the voltages are provide through the accessory from a power source. Before measuring the second voltage, the host device may send an instruction to the accessory instructing the accessory to alter an impedance of the power path between the power source and the host device, and the host device may draw at least a threshold amount of current from the power source via the accessory. The host device may then determine whether the accessory includes particular circuitry based on the relationship between the first voltage and the second voltage.

20 Claims, 18 Drawing Sheets

(56) References Cited

U.S. PATENT DOCUMENTS

| | | | |
|---|---|---|---|
| 5,859,522 A | 1/1999 | Theobald | |
| 6,025,695 A | 2/2000 | Friel et al. | |
| 6,232,764 B1* | 5/2001 | Rettig et al. | 324/115 |
| 7,024,230 B2* | 4/2006 | Curtiss et al. | 455/569.1 |
| 7,170,259 B2 | 1/2007 | Veselic | |
| 7,271,568 B2 | 9/2007 | Purdy et al. | |
| 7,379,311 B2* | 5/2008 | Shih | 363/52 |
| 7,532,492 B2* | 5/2009 | Dobyns et al. | 363/59 |
| 7,627,128 B2* | 12/2009 | Sander et al. | 381/74 |
| 7,627,168 B2* | 12/2009 | Hamburg | 382/163 |
| 7,884,571 B2 | 2/2011 | Veselic | |
| 8,299,773 B2* | 10/2012 | Jang et al. | 323/299 |
| 8,473,761 B2* | 6/2013 | Rathi et al. | 713/300 |
| 8,683,090 B2 | 3/2014 | Mullins et al. | |
| 2004/0103223 A1* | 5/2004 | Gabehart et al. | 710/2 |
| 2005/0268000 A1* | 12/2005 | Carlson | 710/15 |
| 2006/0045112 A1 | 3/2006 | Laiho | |
| 2007/0143638 A1* | 6/2007 | Dobyns et al. | 713/300 |
| 2007/0234420 A1 | 10/2007 | Novotney et al. | |
| 2007/0271400 A1 | 11/2007 | Lernke et al. | |
| 2008/0086651 A1* | 4/2008 | Lunsford et al. | 713/320 |
| 2008/0119241 A1 | 5/2008 | Dorogusker et al. | |
| 2008/0185995 A1 | 8/2008 | Carrier et al. | |
| 2008/0252173 A1* | 10/2008 | Yoshida et al. | 310/317 |
| 2009/0091422 A1 | 4/2009 | Minoo et al. | |
| 2009/0177906 A1 | 7/2009 | Paniagua, Jr. et al. | |
| 2009/0267613 A1 | 10/2009 | Terlizzi et al. | |
| 2010/0173673 A1 | 7/2010 | Lydon | |
| 2010/0201308 A1 | 8/2010 | Lindholm | |
| 2010/0235546 A1* | 9/2010 | Terlizzi et al. | 710/16 |
| 2011/0045323 A1* | 2/2011 | Ooi et al. | 429/50 |
| 2011/0055407 A1* | 3/2011 | Lydon et al. | 709/228 |
| 2011/0163701 A1 | 7/2011 | Carrier et al. | |
| 2011/0167281 A1* | 7/2011 | Rathi et al. | 713/310 |
| 2011/0167287 A1 | 7/2011 | Walsh et al. | |
| 2011/0181235 A1 | 7/2011 | Walley et al. | |
| 2011/0221604 A1 | 9/2011 | Johnson | |
| 2012/0051554 A1 | 3/2012 | Modi et al. | |
| 2012/0054509 A1* | 3/2012 | Rathi et al. | 713/300 |
| 2012/0187905 A1 | 7/2012 | Kanayama | |
| 2012/0198183 A1* | 8/2012 | Wetzel et al. | 711/154 |
| 2012/0221869 A1* | 8/2012 | Rathi et al. | 713/300 |
| 2012/0235636 A1 | 9/2012 | Partovi | |
| 2013/0057216 A1 | 3/2013 | Ribich | |
| 2013/0082662 A1 | 4/2013 | Carre et al. | |
| 2013/0127402 A1 | 5/2013 | Pulijala | |
| 2013/0215578 A1* | 8/2013 | Stronks et al. | 361/749 |
| 2013/0275779 A1* | 10/2013 | He | 713/300 |
| 2013/0278205 A1 | 10/2013 | Mullins et al. | |
| 2013/0279055 A1 | 10/2013 | Mullins et al. | |
| 2013/0305066 A1 | 11/2013 | Mullins et al. | |

OTHER PUBLICATIONS

International Search Report and Written Opinion for PCT Application No. PCT/US2013/035440, mailed Jun. 11, 2013, 17 pages.

Non-Final Office Action for U.S. Appl. No. 13/730,667, mailed Jul. 1, 2013, 14 pages.

Notice of Allowance for U.S. Appl. No. 13/607,473, mailed on Nov. 13, 2013, 22 pages.

Final Office Action for U.S. Appl. No. 13/730,667, mailed Nov. 15, 2013, 20 pages.

Supplemental Notice of Allowability for U.S. Appl. No. 13/607,473, mailed on Nov. 19, 2013, 5 pages.

Notice of Allowance for U.S. Appl. No. 13/730,667, mailed Jun. 11, 2014, 7 pages.

* cited by examiner

| ACC1 | Data A+ | Data A- | P_IN | P_IN | Data B- | Data B+ | ACC2 |
|------|---------|---------|------|------|---------|---------|------|
| 806(1) | 806(2) | 806(3) | 806(4) | 806(5) | 806(6) | 806(7) | 806(8) |

| GND | Data A+ | Data A- | ACC1 | P_IN | Data B- | Data B+ | ACC2 |
|-----|---------|---------|------|------|---------|---------|------|
| 806(1) | 806(2) | 806(3) | 806(4) | 806(5) | 806(6) | 806(7) | 806(8) | ns # METHODS, SYSTEMS AND APPARATUS FOR DETERMINING WHETHER AN ACCESSORY INCLUDES PARTICULAR CIRCUITRY

CROSS-REFERENCES TO RELATED APPLICATIONS

This application is a continuation application that claims priority to U.S. application Ser. No. 13/607,473, filed Sep. 7, 2012, and entitled "METHODS, SYSTEMS AND APPARATUS FOR DETERMINING WHETHER AN ACCESSORY INCLUDES PARTICULAR CIRCUITRY," which claims the benefit of U.S. Provisional Patent Application No. 61/635,652, filed Apr. 19, 2011, and entitled "METHODS, SYSTEMS AND APPARATUS FOR DETERMINING WHETHER AN ACCESSORY INCLUDES PARTICULAR CIRCUITRY," each of which is incorporated herein by reference in its entirety for all purposes. This application is also related to U.S. patent application Ser. No. 13/607,478, filed Sep. 7, 2012 and entitled "METHODS, SYSTEMS AND APPARATUS FOR ENABLING AN ACCESSORY FOR USE WITH A HOST DEVICE," which is incorporated herein by reference in its entirety for all purposes.

BACKGROUND

Embodiments of the present invention generally relate to host devices and accessories. More particularly, embodiments of the present invention relate to techniques for determining whether an accessory includes particular circuitry as well as techniques that enable a power path between a power source and a host device.

Cables are one type of accessory that are often used to connect a host device, such as a mobile phone, a personal digital assistant, a mobile computer, etc. to a power source. The cable may then operate to transfer power from the power source to the host device so as to charge the host device, provide operating power to the host device, and the like. Other types of accessories, such as docking stations, similarly operate to transfer power from a power source to the host device by way of connecting the host device to the accessory. This may be done, for example, by connecting a connector of the host device to a connector of the accessory.

As a result of their power transferring functionality, such cables and other accessories inherently provide a risk of injury to users by, for example, electric shock. Such risks may increase due to particular connector designs (e.g., where the cable or other accessories have a connector with exposed leads for connecting to the host device), due to increased voltages and currents which may be desired to, e.g., increase a charging speed of the host device, and/or due to sub-par quality of manufacturing of the accessories. Such cables and accessories may similarly provide a risk of damage to devices connected thereto. In many instances, these risks also exist due to cables or other accessories maintaining a voltage potential even after being disconnected from the host device.

Accordingly, it is desirable to provide systems, methods, and apparatus that reduce the likelihood of electrical shock resulting from use of such accessories.

SUMMARY

Embodiments of the present invention are generally directed to host devices and accessories and methods of operating host devices and accessories. In particular some embodiments of the present invention are directed to determining whether an accessory includes particular circuitry, such as power limiting circuitry, and operating a host device based on whether the accessory includes the particular circuitry. Some embodiments are also directed to establishing power paths between power sources and host devices.

In accordance with some of the methods described herein, a host device may be operable to determine whether an accessory includes particular circuitry. This may be done by measuring, at a host device coupled to an accessory, a first voltage received from the accessory via a power pin provided in the host device. The host device may then send an instruction to the accessory to alter an impedance, at the accessory, of a power path between a power source and the host device, and then measure a second voltage received from the accessory via the power pin provided in the host device. The host device may then determine whether the accessory includes particular circuitry based on the relationship between the first voltage and the second voltage.

In accordance with other embodiments for determining whether an accessory includes particular circuitry, a method includes measuring, at a host device coupled to an accessory, a first voltage received from the accessory via a power pin provided in the host device. The host device may then sink current from a power source via the accessory, and measure a second voltage received from the accessory via the power pin provided in the host device. The host device may then determine whether the accessory includes particular circuitry based on the relationship between the first voltage and the second voltage.

In addition to the methods of operating host devices and appliances described herein, embodiments are also directed to host devices. Host devices according to various embodiments may include a number of elements, such as power pins, data pins, and control circuitry. For example, a power pin may be operable to receive a voltage from an accessory. A data pin may be operable to communicate various instructions to the accessory. The control circuitry may be operable to perform a variety of functions, such as measuring voltages received via the power pin, sending instructions to the accessory via the data pin instructing the accessory to alter an impedance, at the accessory, of a power path between a power source and the host device, and sinking current from the power source via the accessory. The control circuitry may also be operable to determine whether the accessory includes particular circuitry based on the measured voltages.

In addition to the embodiments directed to various methods and to host devices, embodiments are also directed to accessories. Accessories according to various embodiments may include a number of elements, such as power pins, data pins, and power limiting circuitry. The power pin may be operable to provide a voltage to a host device. The data pin may be operable to receive various instructions communicated from the host device. The power limiting circuitry may be operable to alter an impedance of a power path between a power source and the host device in response to receiving an instruction from the host device, and reduce the voltage provided to the host device from the power source when a threshold amount of current is drawn through the power limiting circuitry.

For a fuller understanding of the nature and advantages of embodiments of the present invention, reference should be made to the ensuing detailed description and accompanying drawings. Other aspects, objects and advantages of the invention will be apparent from the drawings and detailed description that follows. However, the scope of the invention will be fully apparent from the recitations of the claims.

DETAILED DESCRIPTION

Figure 1:
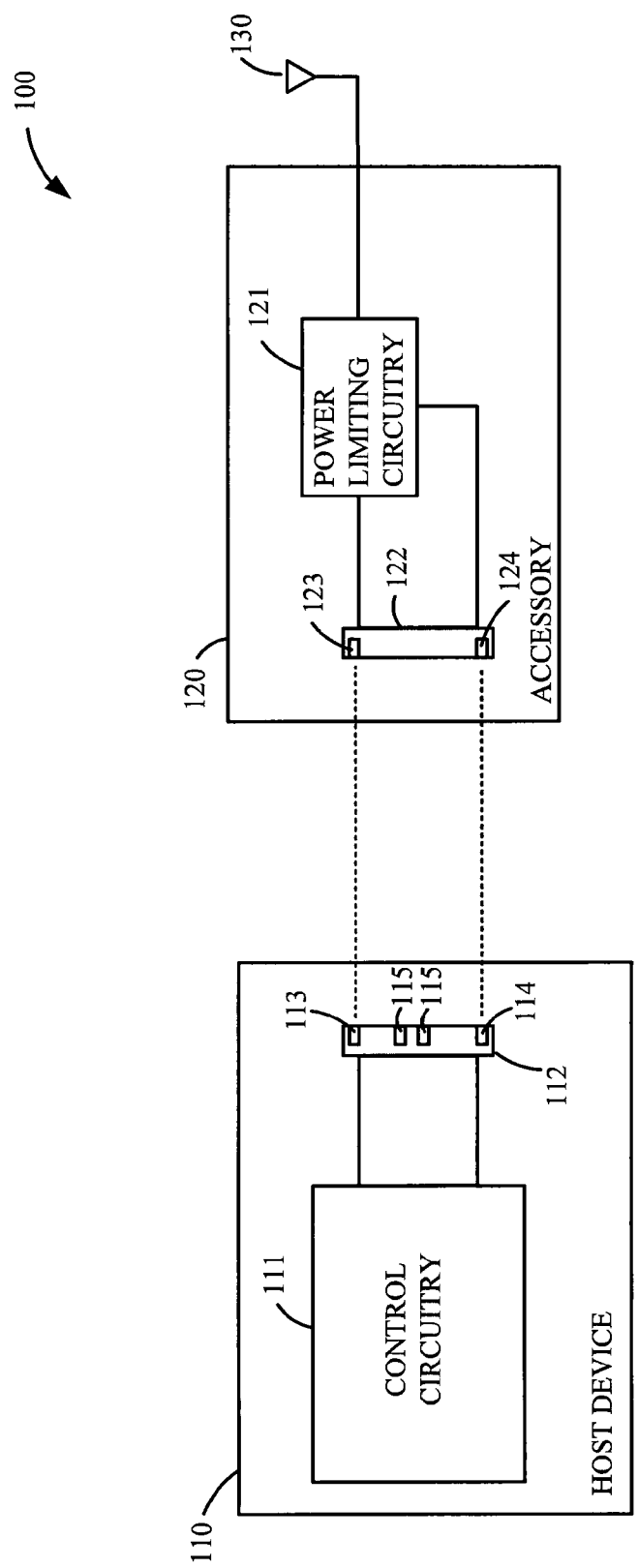
FIG. 1 is a schematic of a system for determining whether an accessory includes particular circuitry according to an embodiment of the present invention.

Embodiments of the invention are discussed below with reference to FIGS. 1 to 12F. However, those skilled in the art will readily appreciate that the detailed description given herein with respect to these figures is for explanatory purposes only as embodiments of the invention extend beyond these limited embodiments.

Systems, apparatus, and methods described herein are generally related to controlling host devices and accessories, and in some cases determining whether an accessory includes particular circuitry such as power limiting circuitry.

"Accessory" should be broadly construed to include any one or more of a variety of electronic components, such as a cable, a docking station, an alarm clock, a radio, a speaker set, a charging station, etc. In general, an accessory can be any device that is operable to be used with a host device. In some embodiments, the accessory may include hardware and/or software operable to influence a power path between the host device (e.g., an iPhone™) and a power source. In some cases, the power source may be included in the accessory (e.g., when the accessory is a charging station), and in other cases the power source may be external to the accessory (e.g., when the accessory is a cable). Accordingly, the accessory may actively provide power or passively transfer power supplied from an external power source.

In some embodiments, a host device may determine whether an accessory includes particular circuitry such as power limiting circuitry and then perform various operations based on the result of such a determination. For example, the host device may refuse to charge via the accessory if the accessory does not include power limiting circuitry. In such cases, the use of accessories which may increase risks of harm to users and damage to host devices may advantageously be reduced.

Whether an accessory includes particular circuitry may be determined using any one or more of the techniques disclosed herein. In general, methods for determining whether the accessory includes particular circuitry may be based on the host device selectively measuring an electrical characteristic, such as an impedance, of the accessory. In one particular embodiment, this characteristic may be measured by first measuring a property of the accessory, then sending an instruction to the accessory for the accessory to change one or more of its properties (e.g., increase its impedance), and then measuring the property of the accessory once again to see whether the accessory understood the instruction and includes the proper circuitry for changing its properties. In some embodiments, the host device may include a current sink to force a certain current to be drawn through the accessory, whereby the host device may then determine whether the accessory includes the particular circuitry as the current sink will place the accessory into a known state (if it includes the particular circuitry).

Once it is determined whether an accessory includes the particular circuitry, the host device may perform additional operations. In some embodiments, power consumption by the host device from the power source may be controlled based on this determination. For example, if it is determined that the accessory includes power limiting circuitry having certain characteristics, the host device may receive power from the power source via the accessory, perhaps for operating internal circuitry of the host device and/or charging an internal battery of the host device. On the other hand, if it is determined that the accessory does not include the power limiting circuitry, the host device may refuse to receive power from the power source via the accessory. In this fashion, the host device may only charge and/or operate with accessories determined to include power limiting circuitry so as to advantageously reduce the likelihood of consumer use of accessories that may not satisfy desired specifications.

Also described herein are techniques for establishing a connection between a host device and an accessory. Such techniques may be used to, for example, facilitate communication between the host device and the accessory and/or establish a power path between a power source and the host device via the accessory. In one embodiment, the host device may send requests for an accessory identifier on a first data pin of the host device and if a valid accessory identifier is not received in response thereto the host device may try sending such requests again on a second data pin different from the first data pin. On the other hand, if a valid accessory identifier is received, the host device may begin to receive power from a power source via the accessory. In some cases, while the host device may begin to receive power after receiving a valid accessory identifier, the host device may then either continue or discontinue receiving such power after determining whether the accessory includes power limiting circuitry.

Turning now to the figures, FIG. 1 is a schematic of a system 100 for determining whether an accessory includes particular circuitry according to an embodiment of the present invention. In this embodiment, system 100 includes a host device 110, an accessory 120, and a power source 130.

Host device 110 may be any suitable electronic device that is operable to perform the functionality discussed herein, and may include one or more hardware and or software components operable to perform such functionality. For example, host device 110 may be a mobile phone, a personal digital assistant (PDA), a handheld or portable device (e.g., iPhone™, Blackberry™, etc.), a notebook, a personal computer, a note pad, a tablet computer, a media player (e.g., a music player or video player), a camera, a game player, a laptop computer, a netbook, a booklet, or other electronic device configured for wired or wireless communication.

Host device 110 includes control circuitry 111 and a connector 112, where control circuitry 111 is electrically coupled to connector 112 and operable to perform some or all of the operations discussed herein with reference to host device 110. Host device 110 may include additional components (not shown), such as a tangible computer-readable storage medium, power source (e.g., a battery), etc., such that host device 110 may be operable to perform one or more of the functions discussed herein either in hardware and/or via instructions stored on the storage medium executed by control circuitry 111. Connector 112 includes one or more pins electrically coupled to control circuitry 111, such as a power pin 113, a data pin 114, and one or more additional data pins 115. In some embodiments, power pin 113 may be electrically and/or mechanically coupled to control circuitry 111 so as to communicate a voltage or other power to control circuitry 111 provided by accessory 120. Data pin 114 may also be electrically and/or mechanically coupled to control circuitry 111 so as to facilitate data communication between control circuitry 111 and accessory 120. The one or more additional data pins 115 may also be electrically and/or mechanically coupled to control circuitry 111 so as to facilitate data communication between control circuitry 111 and accessory 120. In some embodiments, data pin 114 may be arranged to couple to power limiting circuitry 121 of accessory 120, while the one or more additional data pins 115 may be arranged to also couple to power limiting circuitry 121 or different circuitry of accessory 120.

Accessory 120 may be any suitable electronic device that is operable to perform the functionality discussed herein, and may include one or more hardware and or software components operable to perform such functionality. For example, accessory 120 may be a cable, an alarm clock, a radio, a speaker set, a docking station, an input device such as a keyboard, a musical instrument such as a digital piano, a battery, a charging station, an image/video projection unit, or other device operable to source power to the host device or transfer power to the host device provided by a power source external to the accessory.

Accessory 120 includes power limiting circuitry 121 and a connector 122. Accessory 120 may include additional components (not shown), such as a tangible computer-readable storage medium, power source, etc., such that accessory 120 may be operable to perform one or more of the functions discussed herein either in hardware and/or via instructions stored on the storage medium executed by a processor. Connector 122 includes one or more pins electrically coupled to power limiting circuitry 121, such as a power pin 123 and a data pin 124. In some embodiments, power pin 123 may be electrically and/or mechanically coupled to power limiting circuitry 121 so as to communicate a voltage or other power from power limiting circuitry 121 to power pin 113 upon engagement of connector 122 with connector 112. Data pin 124 may also be electrically and/or mechanically coupled to power limiting circuitry 121 so as to establish data communication between power limiting circuitry 121 of accessory 120 and control circuitry 111 of host device 110 upon engagement of connector 122 with connector 112.

Power source 130 may be any type of device operable to source power, voltage, and/or current, such as a battery, an AC/DC converter, an AC electrical outlet, a power supply, etc. Power source 130 may be internal or external to accessory 120. In FIG. 1, power source 130 is depicted as being external to accessory 120. In any case, power source 130 is provided such that power limiting circuitry 121 is disposed in a power path between power source 130 and host device 110. For example, power limiting circuitry 121 may be electrically and/or mechanically disposed between power source 130 and power pin 123 of connector 122.

Host device 110 and accessory 120 may be operable to perform a variety of functions as discussed herein. In one embodiment, host device 110 may be operable to establish a connection with accessory 120, determine whether accessory 120 includes power limiting circuitry 121, and then based on the outcome of that determination perform various actions. For example, upon establishing a connection with accessory 120, host device 110 may receive power from power source 130 via accessory 120. Then, upon determining whether accessory 120 includes power limiting circuitry 121, host device 110 may decide to either continue receiving power from power source 130 or discontinue receiving power from power source 130. In such a fashion, host device 110 may be controlled based on whether or not accessory 120 includes specific circuitry having specific properties.

To establish a connection with accessory 120, in one particular embodiment, upon physically engaging host device 110 and accessory 120 by coupling connector 122 with connector 112, control circuitry 111 may send a request for an accessory identifier to accessory 120 via data pin 114. Control circuitry 111 may then monitor data pin 114 to determine whether a valid accessory identifier is received from accessory 120. If not, control circuitry 111 may re-send the request. In some embodiments, the request may be re-sent on another data pin (such as one of additional data pins 115). For example, connector 112 and connector 122 may have multiple connection orientations whereby they may be physically connected with one another in more than one orientation. In some cases, in a first orientation data pin 114 may be in contact with data pin 124. In a second orientation, data pin 114 may not be in contact with data pin 124, but another data pin such as an additional data pin 115 may be in contact with data pin 124.

At accessory 120, power limiting circuitry 121 may monitor data pin 124 for power and/or requests. For example, in one embodiment, power may be communicated from host device 110 to accessory 120 via data pin 124. This power may be used for accessory 120 to operate in the event accessory 120 cannot acquire operating power from other sources such as power source 130 or does not have an internal power source. If power is not received, then power limiting circuitry 121 may continue to monitor data pin 124. However, if power is received, then power limiting circuitry 121 may disable a power path between power source 130 and host device 110. In some cases, the power path may be disabled by default, and thus further disabling may be omitted. Once the power path is disabled, power limiting circuitry 121 may receive and read the request for an accessory identifier. If the request is valid, then power limiting circuitry 121 may send an accessory identifier to host device 110 via data pin 124, and enable (or re-enable) the power path between power source 130 and host device 110. Otherwise, power limiting circuitry 121 may continue to monitor data pin 124.

Once a connection has been established between host device 110 and accessory 120, the power path between power source 130 and host device 110 may be enabled. In some embodiments, this may allow host device 110 to acquire an operating charge, such as when the host device 110 does not have sufficient power to operate a main processor to execute software provided in the host device 110 (e.g., it has a dead battery). In other embodiments, host device 110 may have sufficient power to operate such software, in which case it may choose to continue operating using its own power or begin to operate using power supplied via the newly enabled power path. In any case, once host device 110 is provided with operating power, host device 110 may determine whether accessory 120 includes power limiting circuitry 121. To do this, control circuitry 111 may measure a first voltage received from accessory 120 via, for example, power pin 113. This first voltage sets a baseline for comparison. Control circuitry 111 may then send an instruction to the accessory to alter its impedance (e.g., alter the impedance, at the accessory, of a power path between power source 130 and host device 110) and/or sink current from power source 130 via accessory 120. The instruction may be sent via data pin 114, while current may be sinked via power pin 113. Once control circuitry 111 performs one or both of these functions, control circuitry 111 may then measure a second voltage received from accessory 120 via power pin 113. The first voltage may then be compared with the second voltage to determine whether accessory 120 includes power limiting circuitry 121. If the first voltage is greater than or less than the second voltage, control circuitry 111 may determine that accessory 120 includes power limiting circuitry 121. Otherwise, control circuitry 111 may determine that accessory 120 does not include power limiting circuitry 121.

If accessory 120 includes power limiting circuitry 121, accessory 120 may understand and respond to the instructions sent by control circuitry 111. For example, power limiting circuitry 121 may receive an instruction, via data pin 124, for accessory 120 to alter an impedance of the power path between power source 130 and host device 110. In response to receiving this instruction, power limiting circuitry 121 may alter the power path impedance.

Figure 2:
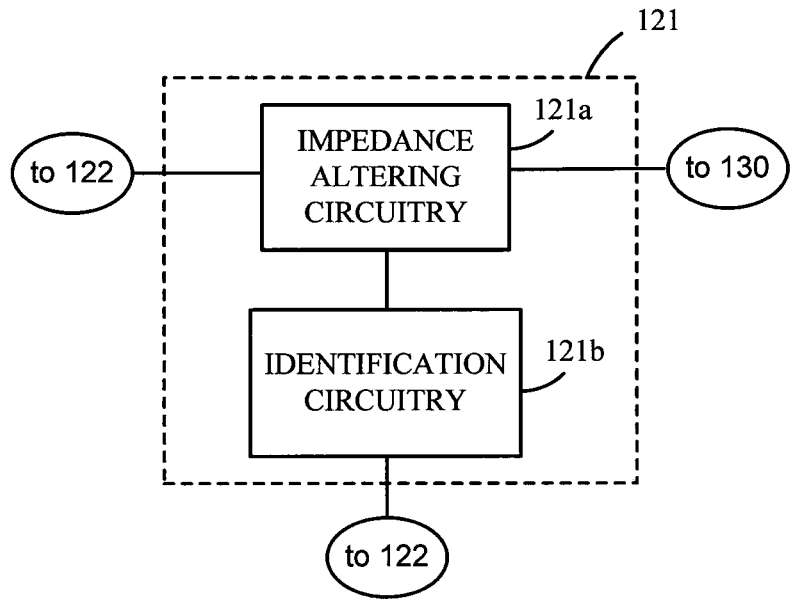
FIG. 2 is a schematic of power limiting circuitry according to an embodiment of the present invention.

In some embodiments, power limiting circuitry 121 may comprise a number of different circuits operable to perform different functions. For example, turning to FIG. 2, FIG. 2 is a schematic of power limiting circuitry according to an embodiment of the present invention. In accordance with an embodiment, power limiting circuitry 121 includes both impedance altering circuitry 121a and identification circuitry 121b. Impedance altering circuitry 121a may be disposed in the power path between power source 130 and host device 110, whereas identification circuitry 121b may be disposed between impedance altering circuitry 121a and data pin 124.

Identification circuitry 121b, which may be implemented at least partially in hardware or software as a processor or other type of logic, may be operable to receive power and data from host device 110 via data pin 124 and respond to the received data. For example, identification circuitry 121b may have stored therein an accessory identifier, and may be operable to communicate the accessory identifier to host device 110 in response to receiving a request for the accessory identifier. Identification circuitry 121b may also be operable to send instructions to impedance altering circuitry 121a instructing impedance altering circuitry 121a to alter an impedance of the power path between power source 130 and host device 110.

Impedance altering circuitry 121a, which may be implemented at least partially in hardware or software as a processor or other type of logic, may be operable to alter an impedance of the power path between power source 130 and host device 110. This may be in response to an instruction from identification circuitry 121b or, in some embodiments, in response to an instruction sent directly from host device 110. There are various ways that impedance altering circuitry 121a may alter the impedance of the power path, as further described herein.

Figure 3:
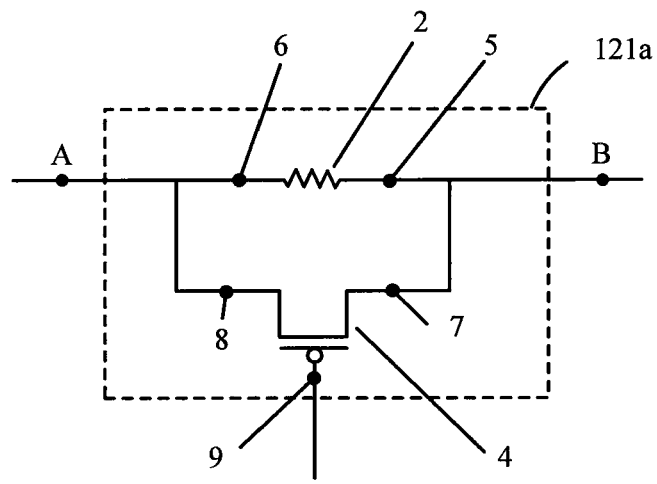
FIG. 3 is a schematic of impedance altering circuitry according to an embodiment of the present invention.

Turning to FIG. 3, FIG. 3 is a schematic of impedance altering circuitry 121a according to one embodiment of the present invention. Impedance altering circuitry 121a according to this embodiment includes a resistive element 2 coupled in parallel with a switch 4 where both are arranged in a power path between points A and B. Resistive element 2 may provide any suitable resistance for measurably altering an impedance characteristic of power limiting circuitry 121a. For example, resistive element 600 may have a resistance of 1 Ohm, 2 Ohm's, 3 Ohm's, 100 Ohm's, 200 Ohm's, 300 Ohm's, 1 kOhm, 2 kOhm's, 3 kOhm's, 1 MOhm, 2 MOhm's, 3 MOhm's, be in a range from 1 to 3 Ohm's, 100 Ohm's to 300 Ohm's, 1 kOhm to 3 kOhm, 1MOhm to 3 MOhm's, or less than 1 Ohm or greater than 3 MOhm's. Resistive element 2 includes a first end 5 that may be coupled to power source 130, and a second end 6 that may be coupled to power pin 123 of connector 122, such that resistive element 2 is disposed in a power path between power source 130 and host device 110.

Switch 4 may be any suitable switching element that allows current provided from power source 130 to selectively bypass resistive element 2. For example, switch 4 may be a MOSFET, JFET, or other type of transistor or other semiconductor device operable to switch electronic signals and power. Switch 4 is coupled in parallel to resistive element 2 and includes a first terminal 7 (e.g., a source) coupled to first end 5 of resistive element 2, a second terminal 8 (e.g., a drain) coupled to second end 6 of resistive element 2, and a third terminal 9 (e.g., a gate) for controlling the operation of switch 4. In some embodiments, first terminal 7 is coupled to power source 130, second terminal 8 is coupled to power pin 123, and third terminal 9 is coupled to data pin 124 of connector 122. Switch 4, when in an OFF state, has a resistance significantly higher than the resistance of resistive element 2. When in an ON state, switch 4 has a resistance that is significantly lower than the resistance of resistive element 2.

As mentioned, power limiting circuitry 121 (e.g., impedance altering circuitry 121a) may operate to alter an impedance of a power path between power source 130 and host device 110. In some embodiments, power limiting circuitry 121 may operate in different modes, such as in a bypass mode and a power limiting mode. Such modes may be entered in response to instructions from host device 110 and, in some embodiments, power limiting circuitry 121 may operate in some modes (e.g., the power limiting mode) by default. Operating by default in power limiting mode may advantageously reduce user risk to exposed voltage potentials, such as when connector 122 of accessory 120 is not connected to connector 112 of host device 110.

Figure 4:
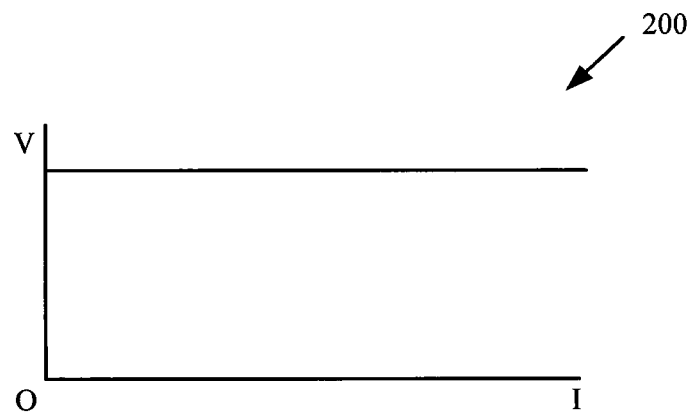
FIG. 4 is a graph illustrating a voltage/current characteristic of power limiting circuitry operating in a bypass mode according to an embodiment of the present invention.

Turning briefly to FIG. 4, FIG. 4 is a graph illustrating a voltage/current characteristic 200 of power limiting circuitry 121 (e.g., impedance altering circuitry 121a) operating in a bypass mode according to an embodiment of the present invention. While operating in the bypass mode, impedance altering circuitry 121a may operate to allow current and voltage to pass through impedance altering circuitry 121a substantially unaltered. Accordingly, any current and voltage supplied to impedance altering circuitry 121a from power source 130 will similarly be supplied to host device 110. For example, power source 130 may supply 5V to impedance altering circuitry 121a. In the bypass mode, impedance altering circuitry 121a may provide the 5V to power pin 123 of connector 122. In some embodiments, a perfect bypass may be not achieved, and thus impedance altering circuitry 121a may have a nominal affect on the power passing therethrough while in bypass mode such as causing a small voltage drop (e.g., a drop of 0.5V, 0.25V, or 0.1V, or in a range from 0.1V to 0.5V, or greater than 0.5V, or less than 0.1V, reduction in current, change in phase, etc.

In one embodiment, the bypass mode may result from switch 4 (FIG. 3) being operated in an ON state. As a result of the relatively low resistance of switch 4 as compared to resistive element 2, current provided from power source 130 may pass through impedance altering circuitry 121a substantially unaltered. Accordingly, a voltage at point A will be substantially similar to that supplied at point B even as an increased amount of current passes through impedance altering circuitry 121a.

Figure 5A:
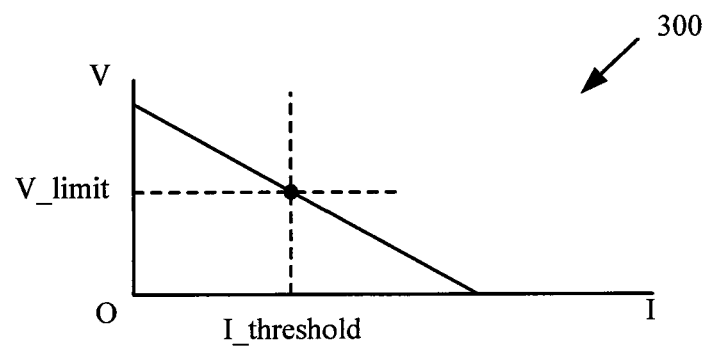
FIG. 5A is a graph illustrating a voltage/current characteristic of power limiting circuitry operating in a power limiting mode according to a first embodiment of the present invention.

Power limiting circuitry 121 (e.g., impedance altering circuitry 121a) may also operate in a power limiting mode. Turning briefly to FIG. 5A, FIG. 5A is a graph illustrating a voltage/current characteristic 300 of power limiting circuitry 121 (e.g., impedance altering circuitry 121a) operating in a power limiting mode according to a first embodiment of the present invention. While in the power limiting mode of operation, impedance altering circuitry 121a may operate to limit an amount of power passed therethrough from power source 130 to host device 110. For example, impedance altering circuitry 121a may limit the amount of voltage provided to host device 110 and, in some cases, impose greater limits on the amount of voltage provided to host device 110 in response to an increasing amount of current being drawn through current limiting circuitry 321.

In one embodiment, this voltage/current characteristic of impedance altering circuitry 121a for the power limiting mode may be achieved by placing switch 4 (FIG. 3) into an OFF state. As a result of the relatively high resistance of switch 4 as compared to resistive element 2, current provided from power source 130 may pass through resistive element 2. Since resistive element 2 has a resistance that is greater than a nominal amount such as 0 Ohms, a voltage at point A will decrease compared to that supplied at point B as an increased amount of current passes through impedance altering circuitry 121a.

Figure 5B:
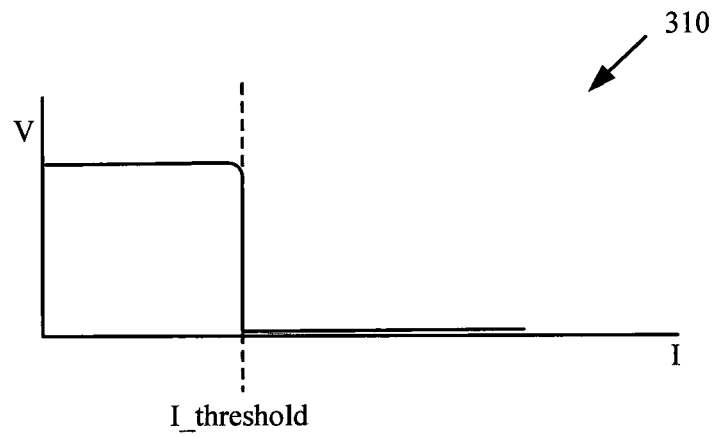
FIG. 5B is a graph illustrating a voltage/current characteristic of power limiting circuitry operating in a power limiting mode according to a second embodiment of the present invention.

It should be recognized that a power limiting mode is not limited to the voltage/current characteristic discussed with reference to FIG. 5A. For example, FIG. 5B is a graph illustrating a voltage/current characteristic 310 of power limiting circuitry 121 (e.g., impedance altering circuitry 121a) operating in a power limiting mode according to a second embodiment of the present invention. In accordance with this embodiment, while operating in the power limiting mode, impedance altering circuitry 121a may operate to reduce a voltage provided by power source 130 if a certain amount of current is drawn through impedance altering circuitry 121a. For example, the voltage may be reduced by a certain amount, such as 1V, 2V, or 3V, in a range from 1V to 3V, by an amount less than 1V or greater than 3V, or the voltage may be reduced to a certain voltage (e.g., 0V, −1V, +1V, −2V, +2V, etc.). In one embodiment and as illustrated in FIG. 5B, the voltage may be reduced to approximately 0V in the event that at least a threshold amount of current, I_threshold, is drawn through impedance altering circuitry 121a.

Switching between the bypass and power limiting modes of operation may result in a predictable change in one or more electrical characteristics of accessory 120. For example, where power limiting circuitry 121 is operable to switch between the bypass and power limiting modes of operation and at least an amount of current equal to or greater than I_threshold (FIG. 5A or 5B) is drawn through power limiting circuitry 121, host device 110 may operate to measure the changes in the electrical characteristics of accessory 120 as a result of the mode switching. In the event the changes in the electrical characteristics resulting from the mode switching satisfy some predetermined threshold, host device 110 may determine that accessory 120 includes power limiting circuitry 121 and may thus determine whether accessory 120 includes particular circuitry.

In accordance with one embodiment, host device 110 may send an instruction to accessory 120 to change operation modes from a bypass mode of operation to a power limiting mode of operation and, if host device 110 detects that accessory 120 successfully changed modes as instructed, host device 110 may determine that accessory 120 includes power limiting circuitry 121. In another embodiment, host device 110 may force an amount of current to be drawn from power limiting circuitry 121 that is greater than or equal to I_threshold via, for example, a current sink located in host device 110. If host device 110 detects that accessory 120 has some electrical characteristic associated with the drawn amount of current (e.g., 0V), host device 110 may determine that accessory 120 includes power limiting circuitry 121. In yet another embodiment, host device 110 may both send an instruction to accessory 120 to change modes of operation and draw an amount of current from power limiting circuitry 121 that is greater than or equal to I_threshold.

Figure 6:
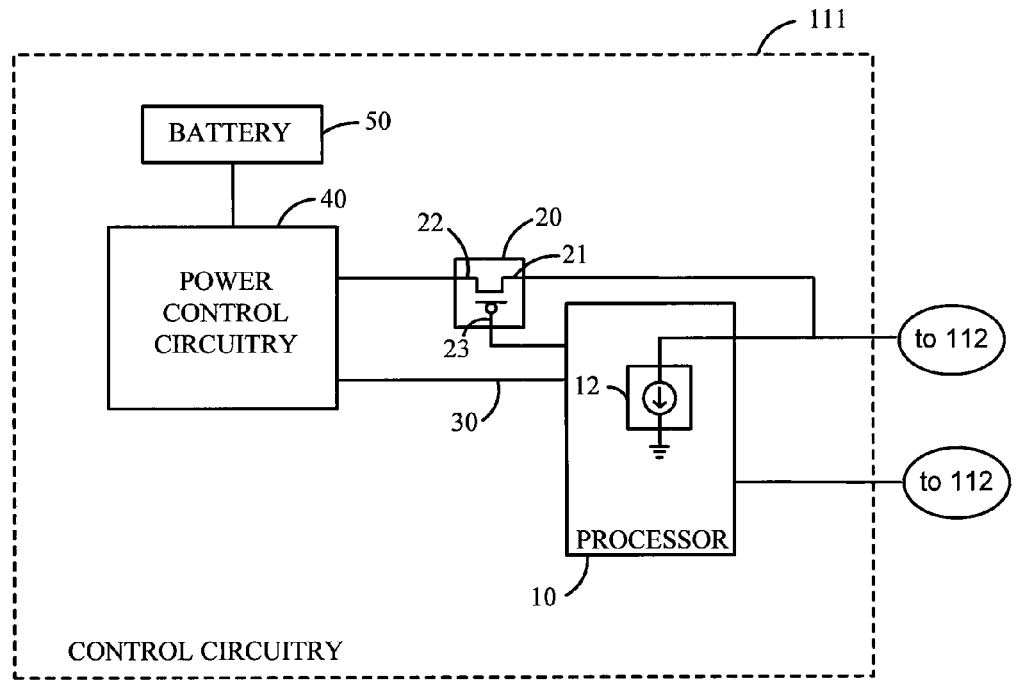
FIG. 6 is a schematic of control circuitry in accordance with an embodiment of the present invention.

Turning our attention now to host device 110, control circuitry 111 may include a number of components operable to perform the functionality discussed herein with reference to host device 110. FIG. 6 is a schematic of control circuitry 111 in accordance with an embodiment of the present invention. In this embodiment, control circuitry 111 includes a processor 10, a current sink 12 (which may or may not be included in processor 10), a charge control switch 20, power control circuitry 40, and a battery 50. Control charge control switch 20 to activate and deactivate charging of battery 50 or other internal circuitry from a power source 130 in response to commands from processor 10, while power control circuitry 40 may operate to protect battery 50 or other internal circuitry from excess voltages passed through charge control switch 20.

Processor 10 may be any suitable computer processor operable to perform the functions described herein, where processor 10 may be operable to perform various functions discussed with reference to control circuitry 111 such as measuring voltages, comparing voltages, sending instructions and receiving responses thereto, etc. Charge control switch 20 may be a MOSFET, JFET, or other type of transistor or other semiconductor device operable to switch electronic signals and power. Charge control switch 20 includes a first terminal 21 (e.g., a source) coupled to current sink 12 and power pin 113, a second terminal 22 (e.g., a drain) coupled to power control circuitry 40, and a third terminal 23 (e.g., a gate) coupled to processor 10. Processor 10 may be operable to change a state of charge control switch 20 via third terminal 23, such as by placing charge control switch 20 into an ON state or an OFF state. When in the ON state, charge control switch 20 may be operable to connect power control circuitry 40 to power pin 113 (FIG. 1), and when in the OFF state, charge control switch 20 may be operable to disconnect power control circuitry 40 from power pin 113. Accordingly, processor 10 may operate to activate or deactivate charging of battery 50 or other internal circuitry from power source 130 by enabling or disabling charge control switch 20. In some embodiments, power control circuitry 40 may be operable to prevent excess voltage from power source 130 from being provided to battery 50 or other internal circuitry.

Figure 7:
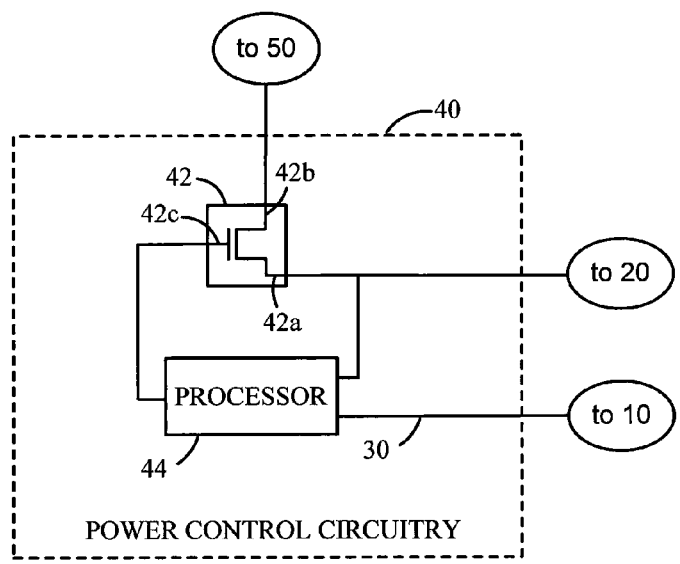
FIG. 7 is a schematic of power control circuitry in accordance with an embodiment of the present invention.

Turning briefly to FIG. 7, FIG. 7 is a schematic of power control circuitry 40 in accordance with an embodiment of the present invention. Power control circuitry 40 includes an overvoltage protection switch 42 and a processor 44. Overvoltage protection switch 42 may be a MOSFET, JFET, or other type of transistor or other semiconductor device operable to switch electronic signals and power. Overvoltage protection switch 42 includes a first terminal 42a (e.g., a source) coupled to second terminal 22 of charge control switch 20, a second terminal 42b (e.g., a drain) coupled to other internal circuitry of host device 110 operable to store a charge provided via accessory 120 (e.g., battery 50), and a third terminal 42c (e.g., a gate) coupled to processor 44.

Processor 44 may be operable to receive information indicating a voltage at first terminal 42a of overvoltage protection switch 42. In some embodiments, processor 44 may include analog-to-digital functionality operable to convert an analog voltage read at first terminal 42a to a digital value. Processor 44 may also be coupled to third terminal 42c of overvoltage protection switch 42 and operable to change a state of overvoltage protection switch 42 via third terminal 42c, such as by placing overvoltage protection switch 42 into an ON state or an OFF state. When in the ON state, overvoltage protection switch 42 may be operable to connect other circuitry that is internal to host device 110 (e.g., battery 50) to second terminal 22 of charge control switch 20, and when in the OFF state, overvoltage protection switch 42 may be operable to disconnect the other internal circuitry from second terminal 22. In operation, processor 44 may place overvoltage protection switch 42 into the OFF state when a voltage at first terminal 42a exceeds a predetermined value, and otherwise place overvoltage protection switch into the ON state.

Further, power control circuitry 40 (e.g., processor 44) may be coupled to processor 10 via a power line 30 that is operable to provide a voltage from power control circuitry 40 to processor 10 so as to power processor 10. In some embodiments, power line 30 may be operable to provide a voltage to processor 10 from an internal charge storage element (e.g., battery 50) of host device 110 regardless of whether host device 110 receives power from power source 130.

System 100 in certain embodiments may be a system for determining whether an accessory includes particular circuitry. However, it will be appreciated by those of ordinary skill in the art that such a system could operate equally well with more or, in some instances, fewer components than are illustrated in FIG. 1. Similarly, it will be appreciated by those of ordinary skill in the art that the schematics illustrated in and discussed with reference to FIGS. 2, 3, 6, and 7 could operate equally well with more or, in some cases, fewer components, and that the characteristics depicted in and discussed with reference to FIGS. 4 through 5B are merely example voltage/current characteristics. Thus, the depictions in FIGS. 1 through 7 should be taken as being illustrative in nature, and not limiting to the scope of the disclosure.

Figure 8A:
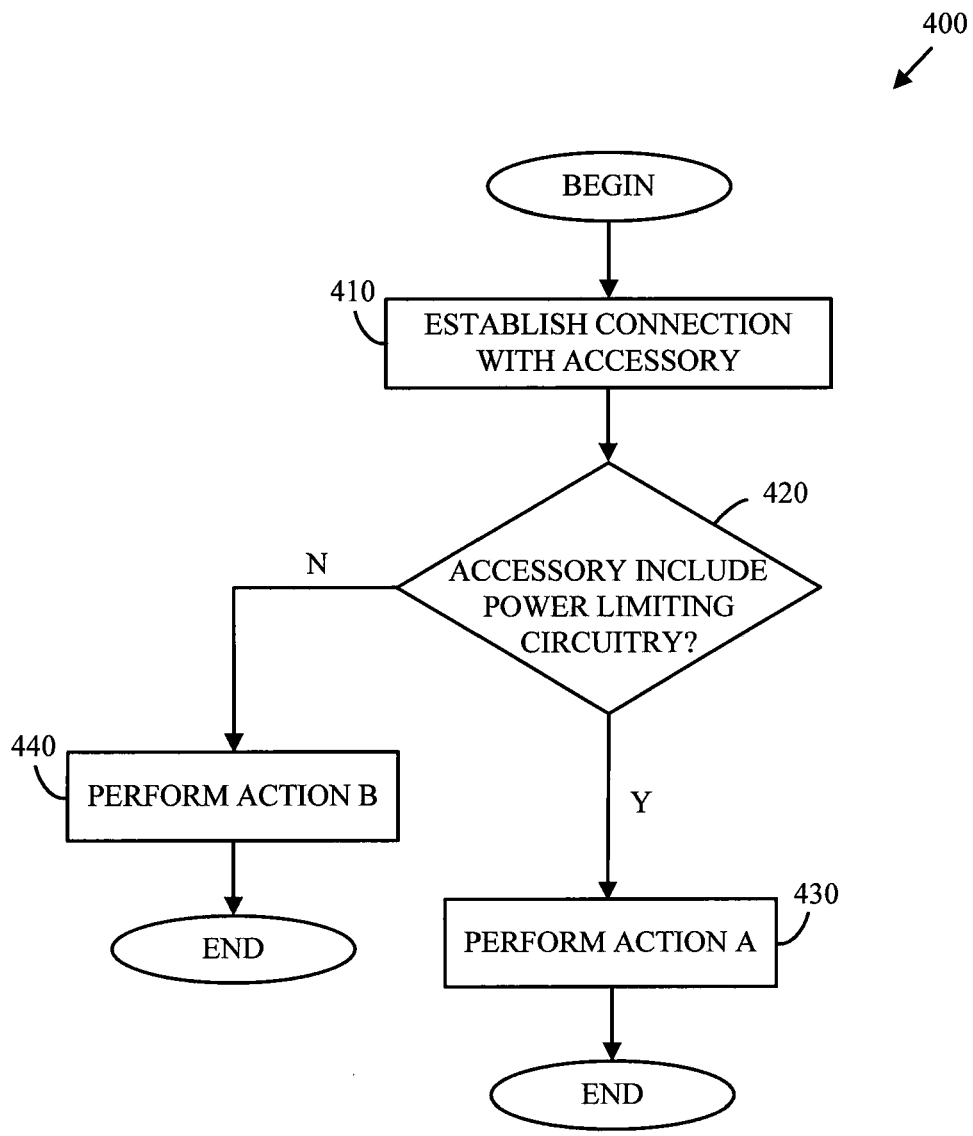
FIG. 8A is a flowchart of a process for operating a host device according to an embodiment of the present invention.

FIG. 8A is a flowchart of a process 400 for operating a host device in accordance with an embodiment of the present invention. Process 400 can be performed by any suitable electronic device such as host device 110 (FIG. 1), but is equally applicable to other electronic devices described herein.

At block 410, the host device (e.g., host device 110) establishes a connection with an accessory (e.g., accessory 120). In establishing a connection with the accessory, the host device and the accessory may initially be physically coupled to one another. For example, connector 112 may mate with connector 122. In some embodiments, the host device and accessory may not physically couple to one another, but may wirelessly couple to one another. For example, each device may include wireless circuitry operable to communicate over wireless networks (e.g., WLAN, IEEE 802.11, etc.), wireless sensor networks (e.g., Bluetooth, Zigbee, etc.), short-range point-to-point communication link (e.g., IrDA, RFID, NFC, etc.).

In some embodiments, establishing a connection may include the host device providing power to the accessory. For example, host device 110 may provide power to accessory 120 over the same data pin used to communicate with accessory 120, where such power may be provided simultaneously with communicating with accessory 120. This may be done to provide accessory 120 with operating power in the event accessory 120 does not have a power source or does not acquire operating power from a power source remote from accessory 120.

In at least one embodiment, establishing a connection with the accessory includes detecting a mechanical connection with the accessory. For example, the host device may monitor a pin in a connector of the host device, such as power pin 113 and/or data pin 114, for a change of impedance, voltage, or other electrical characteristic. Some specific techniques for detecting connection with an accessory are disclosed in commonly-owned and co-pending U.S. patent application Ser.

No. 13/607,550, titled "TECHNIQUES FOR CONFIGURING CONTACTS OF A CONNECTOR", filed on Sep. 7, 2012 the full disclosure of which is incorporated by reference herein in its entirety for all purposes. Once the mechanical connection is detected, the host device may then continue to perform other handshaking operations, such as those discussed with reference to FIG. 8C.

At block 420, the host device determines whether the accessory includes particular circuitry (e.g., power limiting circuitry 121). In determining whether the accessory includes particular circuitry, the host device may determine whether the accessory includes that particular physical circuitry having certain characteristics and/or software modules that perform the functionality of the power limiting circuitry. Some particular embodiments for determining whether the accessory includes particular circuitry are further discussed with reference to FIG. 8D.

If at block 420, the host device determines that the accessory includes the particular circuitry (e.g., power limiting circuitry), the host device performs action "A" at block 430. Action "A" may be one or more of a variety of actions. For example, the host device may begin to accept power from a power source via the accessory (by, e.g., closing charge control switch 20 in FIG. 6, or otherwise coupling power pin 113 to internal charge circuitry). For another example, in the event the host device is already receiving power from the power source via the accessory, the host device may continue to accept power from the power source via the accessory. For yet another example, the host device may communicate information to the user of the host device (via, e.g., a display, audio, or other output unit of the device) or to another computing device (via, e.g,. a wired or wireless network connection) indicating that the accessory includes the particular circuitry or otherwise indicating that the accessory is authorized for use with the host device. In some embodiments, one of more of these actions may be performed simultaneously.

On the other hand, if at block 420 the host device determines that the accessory does not include the particular circuitry, the host device performs action "B" at block 440 which is different than action "A". Action "B" may be one or more of a variety of actions. For example, the host device may refuse to accept power from a power source via the accessory (by, e.g., opening charge control switch 20 in FIG. 6, or otherwise decoupling power pin 113 from internal charge circuitry). For another example, in the event the host device is already receiving power from the power source via the accessory, the host device may then stop accepting power from the power source via the accessory. For yet another example, the host device may communicate information to the user of the host device (via, e.g., a display, audio, or other output unit of the device) or to another computing device (via, e.g,. a wired or wireless network connection) indicating that the accessory does not include the particular circuitry or otherwise indicating that the accessory is not authorized for use with the host device. In some embodiments, one of more of these actions may be performed simultaneously.

Figure 8B:
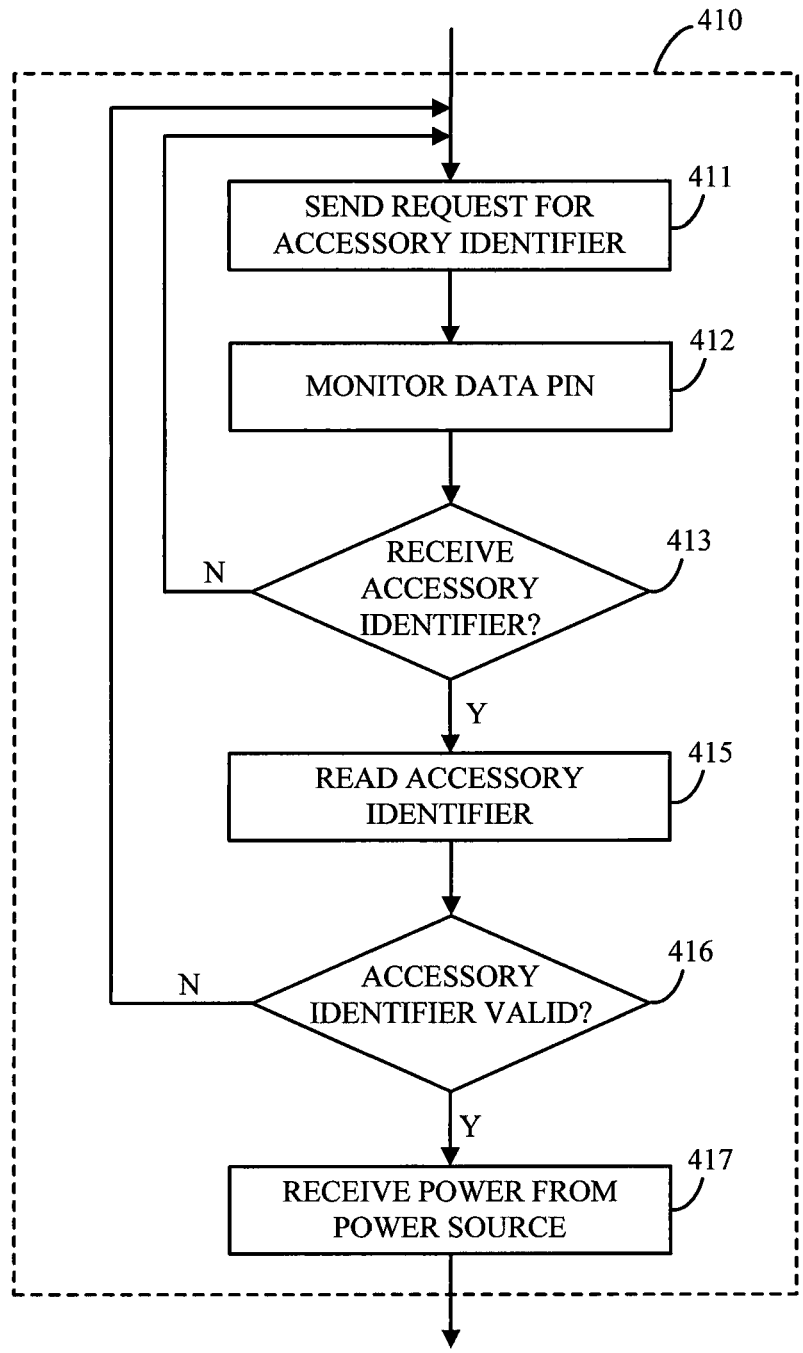
FIG. 8B is a flowchart of a process for a host device to establish a connection with an accessory according to a first embodiment of the present invention.

Turning now to FIG. 8B, FIG. 8B is a flowchart of a process 410 for a host device to establish a connection with an accessory according to a first embodiment of the present invention. Process 410 can be performed by any suitable electronic device such as host device 110 (FIG. 1), but is equally applicable to other electronic devices and accessories described herein. In accordance with some embodiments, process 410 may facilitate or assist in facilitating the establishment of a communication link and/or a power path between a host device and an accessory. This may include sending information from the host device to the accessory on a data pin and, if no response or an unacceptable response is received, re-sending the information on the same data pin. In at least one embodiment, once an acceptable response is received from the accessory, the host device may begin charging or otherwise receiving power provided from a power source via the accessory.

At block 411, the host device sends a request for an accessory identifier to the accessory. The request may be a request for the accessory to send an identifier identifying the device. The accessory identifier may identify one or more suitable characteristics of the accessory. For example, the accessory identifier may include a product name and/or number associated with the accessory, a name and/or number identifying the manufacturer of the accessory, a serial number or other identifier uniquely identifying a particular accessory, a MAC address, IP address, or other network-based identifier associated with the accessory, etc. For another example, the accessory identifier may identify whether the accessory is operable to communicate using one or more of a plurality of communication protocols, such as USB, UART, JTAG, etc., whether the accessory is operable to receive charging power from the host device, etc. In one particular example, the accessory identifier may include pin configuration information that instructs the host device as to which function (e.g., receive charging/operating power, communicate using USB, communicate using ART, etc.) the host device should implement for one or more of its pins of connector 112. Some accessory identifiers are described in the context of response sequences for responding to a request for pin configuration and accessory capability information in U.S. patent application Ser. No. 13/607,426, titled "DATA STRUCTURES FOR FACILITATING COMMUNICATION BETWEEN A HOST DEVICE AND AN ACCESSORY", filed Sep. 7, 2012, the entire contents of which are incorporated herein by reference in their entirety for all purposes.

In some embodiments, the request for an accessory identifier may include information about the host device. For example, the request may include a host identifier, where the host identifier may identify one or more suitable characteristics of the host. For example, like the accessory identifier, the host identifier may include a product name and/or number associated with the host device, a name and/or number identifying the manufacturer of the host device, a serial number or other identifier uniquely identifying a particular host device, a MAC address, IP address, or other network-based identifier associated with the host device, etc.

In at least one embodiment, the request for an accessory identifier may be communicated using one or more of a variety of error detection and, in some embodiments, error correction, techniques. Error detection techniques which may be used include the use of repetition codes, parity bits, checksums, cyclic redundancy checks (CRCs), cryptographic hash functions, error-correcting codes, etc. Accordingly, in some embodiments, the request for an accessory identifier includes error detection information suitable for use in such error detection/correction techniques. For example, the request may include one or more parity bits, checksums, CRC check values, hash function outputs, etc. In some embodiments, the error detection information may be sent separate from the request.

The request may be sent via any suitable mechanism. For example, with reference to FIG. 1, control circuitry 111 may generate and send the request via a data pin such as data pin 114. The request may be sent to any suitable recipient. For example, again with reference to FIG. 1, the host device may send the request to accessory 120. Further, the request may be sent at any suitable time. For example, the host device may be operable to detect a mechanical, electrical, wireless, or other connection with the accessory and, in response to detecting such a connection, send the request via the data pin.

At block 412, the host device monitors the data pin on which it sent the request for an accessory identifier. For example, with reference to FIG. 1, where host device 110 sends a request for an accessory identifier via data pin 114, the host device may then monitor data pin 114. Monitoring may be performed by a processor or other circuitry and/or software in the host device, such as by control circuitry 111. In some embodiments, the host device may monitor other data pins or other communication means (e.g., wireless communication circuitry).

At block 413, the host device determines whether the requested accessory identifier is received. In some embodiments, the host device may determine whether the requested accessory identifier is received on the same pin which the request was sent out on. For example, host device 110 may determine whether the requested accessory identifier is received via data pin 114. In other embodiments, the host device may determine whether the request accessory identifier is received on a different pin or by some other communication means (e.g., wireless).

If at block 413 the host device determines that the requested accessory identifier is not received (e.g., due to a timeout), processing may return to block 411 where another request for an accessory identifier is sent. For example, one or more subsequent requests for accessory identifiers may be sent on data pin 114. In some embodiments, the host device my stop sending requests after a certain number of requests have been sent, after a certain time period has elapsed, or in response to some other condition being satisfied. In other embodiments, the host device may continuously send such requests until a satisfactory response is received.

If at block 413 the host device determines that the requested accessory identifier is received, processing may continue to block 415 where the host device may read the accessory identifier. For example, with reference to FIG. 1, control circuitry 111 may read the accessory identifier received on data pin 114 or another data pin (not shown). In some embodiments, the received accessory identifier may be stored by the host device.

In some embodiments, the host device may use a timer when determining whether an accessory identifier has been received. If the timer has expired before an accessory identifier has been received, then the host device may re-send the request. For example, the host device may initiate a timer after sending the request for an accessory identifier as discussed with reference to block 411. The determination as to whether an accessory identifier has been received, as discussed with reference to block 413, may then be made once the timer has expired. The timer may set to have any suitable duration. For example, the timer may expire after 1 ms, 2 ms, 3 ms, or at a time in the range of 1 ms to 3 ms, or at a time less than 1 ms or greater than 3 ms.

At block 416 the host device determines whether the received accessory identifier is valid. Determining the validity of the received accessory identifier may include one or more of a variety of operations. In one embodiment, the accessory identifier may be communicated using one or more of a variety of error detection and, in some embodiments, error correction, techniques, similar to those discussed above with reference to the request for an accessory identifier. Accordingly, determining the validity of the received accessory identifier may include performing error detection on the accessory identifier. In some embodiments, this may include using error detection information, such as parity bits, check-sums, CRC check values, hash function outputs, etc., communicated with or separate from the accessory identifier. In the event the host device does not detect any errors in the received accessory identifier, the host device may determine that the received accessory identifier is valid. In contrast, in the event the host device detects one or more errors in the received accessory identifier, the host device may determine that the received accessory identifier is not valid. In some embodiments, in the event the host device detects one or more errors in the received accessory identifier, the host device may attempt to correct those errors and subsequently determine that the received accessory identifier is not valid only if it is unable to correct at least one of those errors.

In another embodiment, the received accessory identifier may be compared to a list of authorized accessory identifiers. For example, the host device may have stored therein, or be operable to access from a location remote from the host device, a database including the list of authorized accessory identifiers, where the accessory identifiers provided on the list have been authorized to operate with the host device. By comparing the received accessory identifier to the list of authorized accessory identifiers, the host device may check to see if the received accessory identifier matches one or more of the accessory identifiers provided on the list. In the event of a match, the host device may determine that the received accessory identifier is valid. In contrast, in the event the received accessory identifier does not match any of the accessory identifiers provided on the list, the host device may determine that the received accessory identifier is not valid.

In some embodiments, the accessory identifier may also include control information. The control information may provide one or more parameters to configure the host device to communicate or provide power to the accessory. For example, the control information may instruct the host device to configure itself for USB, UART, or other types of communication with the accessory. In one embodiment and with reference to FIG. 1, connector 112 may include additional pins for communicating with accessory 120 or an electronic device other than accessory 120, such as additional data pins 115. Additional data pins 115 may each be selectively configured to communicate over a number of different communication protocols, such as USB, UART, JTAG, etc. The control information may then instruct the host device to use a particular communication protocol (e.g., one of USB, UART, JTAG, etc.) to communicate over a particular pin (e.g., one of additional data pins 115). As a result, control circuitry 111 may subsequently communicate data to components of accessory 120 (which may include power limiting circuitry 121 or be separate from power limiting circuitry 121) using a communication protocol selected by the accessory 120 over a particular pin selected by accessory 120.

If the host device determines that the received accessory identifier is not valid, processing may return to block 411, where the host device may send another request for an accessory identifier as previously described. In contrast, if the host device determines that the received accessory identifier is valid, processing may continue with block 417.

At block 417, the host device at least temporarily receives power from the power source via the accessory. For example, with reference to FIG. 1, host device 110 may receive power from power source 130 via accessory 120. In one embodiment, host device 110 may receive power from power source 130 that is communicated to power pin 123 of accessory 120 via power limiting circuitry 121, where host device 110 receives the power by power pin 113 of host device 110. For example, in one embodiment, processor 10 (FIG. 6) may communicate a signal to third terminal 23 (FIG. 6) to place charge control switch 20 (FIG. 3) into an ON state such that power from power pin 113 may be communicated to charge circuitry or other internal circuitry of host device 110.

In one embodiment, as a result of placing charge control switch 20 into an ON state, power from power pin 113 may be communicated to power control circuitry 40 (FIG. 6). Power control circuitry 40 may then operate to communicate the power to other circuitry of the host device 110 (e.g., battery 50) if the power is less than some predetermined maximum. For example, if the voltage at first terminal 42*a* (FIG. 7) is less than or equal to a predetermined maximum voltage.

The power received by the host device may be used in any suitable fashion. For example, the host device may use the received power to operate internal circuitry of the host device, and/or to charge an internal battery (e.g., battery 50) of the host device. In this fashion, the host device may only charge and/or operate with accessories providing a valid accessory identifier. It should be recognized, however, that the power received by the host device at this point may only be temporarily accepted and used by the host device. With reference to FIG. 8A, processing then continues to block 420, where the host device may then determine whether the accessory includes power limiting circuitry. In some embodiments, if it is determined that the accessory does not include power limiting circuitry, the host device may stop accepting power received from the accessory. Accordingly, the power received at block 417 may only be temporarily accepted or otherwise used by the host device.

Figure 8C:
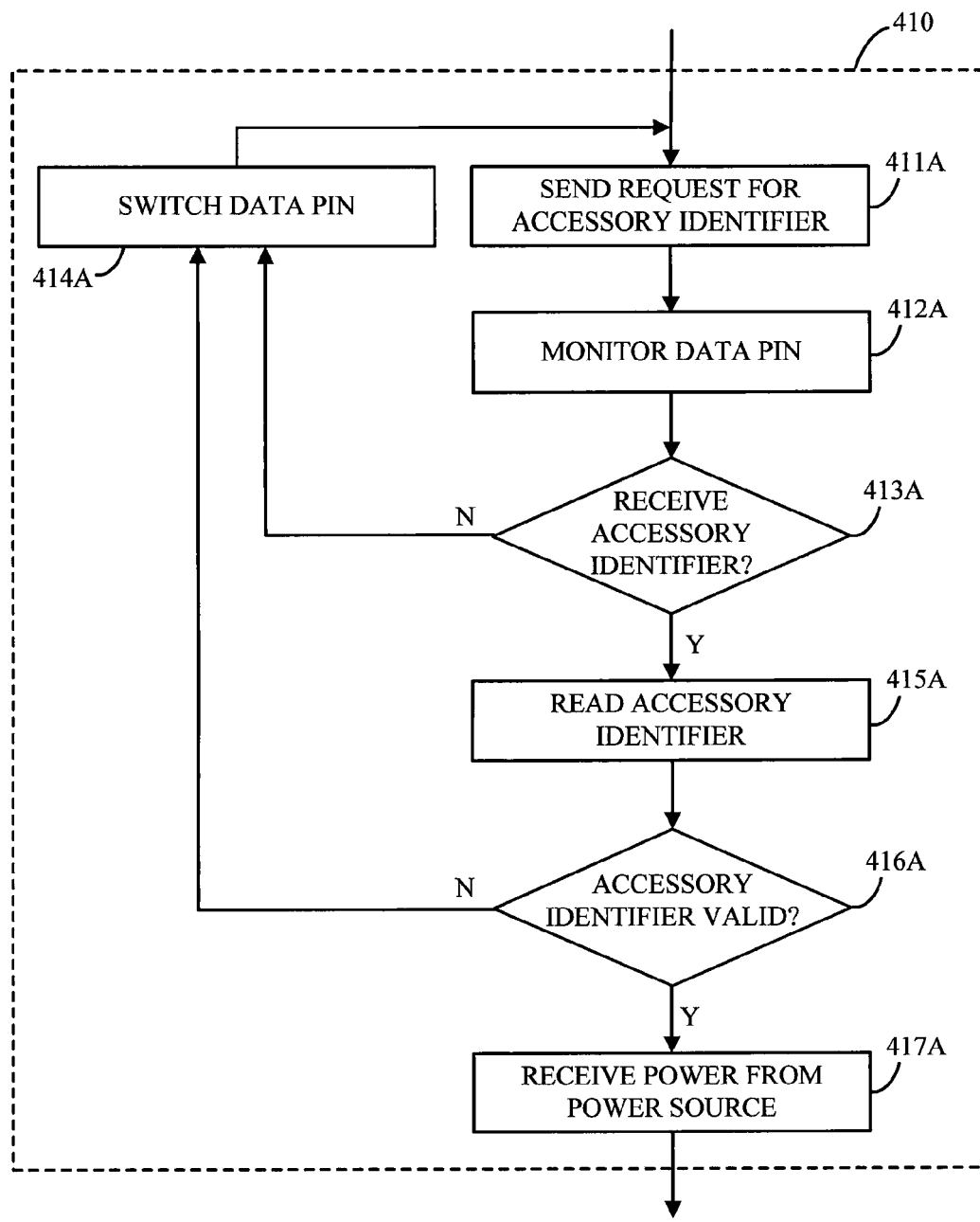
FIG. 8C is a flowchart of a process for a host device to establish a connection with an accessory according to a second embodiment of the present invention.

FIG. 8C is a flowchart of a process 410 for a host device to establish a connection with an accessory according to a second embodiment of the present invention. The operations illustrated in the process of FIG. 8C are the same as those illustrated and discussed with reference to FIG. 8B, where blocks 411A to 417A are substantially the same as the respectively numbered blocks 411 to 417. However, in this embodiment, the host device may switch data pins and send subsequent requests for an accessory identifier on a different data pin. Such a process may be particularly advantageously in embodiments where the connectors are multi-orientation connectors, whereby they may mate together in multiple orientations. However, such a process may also be used in embodiments where the connectors are single-orientation connectors.

As mentioned, blocks 411A to 417A depicted in FIG. 8C are substantially the same as the corresponding blocks 411 to 417 depicted in FIG. 8B, and thus further description is omitted. In this embodiment, however, at block 413A, in response to the host device determining that the requested identifier is not received, processing continues to block 414A. Similarly, at block 416A, in response to the host device determining that the received accessory identifier is not valid, processing continues to block 414A.

At block 414A, the host device switches data pins from the data pin by which the request for an accessory identifier was communicated to a different data pin. For example, with reference to FIG. 1, where host device 110 initially sends a request for an accessory identifier via data pin 114, in the event that the host device determines that the requested accessory identifier is not subsequently received, the host device may then switch data pins from data pin 114 to another data pin (e.g., one of additional data pins 115) provided in connector 112. Upon switching from data pin 114 to another data pin, processing may then return to block 411A, where the host device sends the request for an accessory identifier on the other data pin rather than data pin 114.

In some embodiments, when switching between data pins, the host device may cycle through available pins in any suitable sequence. In some embodiments, the host device may include more than two data pins. The host device may then use all or a subset of those pins to communicate requests for accessory identifiers. For example, the host device may cycle through all of the pins and communicate the request on all of the pins, or the host device may cycle through only a subset of the pins and communicate the request on only the subset of pins. Upon communicating the request on all or only the subset of pins, the host device may then again communicate the request on all or only the subset of pins. The host device may continue to send requests until a satisfactory response is received. In some embodiments, the host device may include only two data pins. In such a case, the host device may alternate between the two data pins such that requests are communicated on each of the pins in a cyclical manner.

In some embodiments and as described with reference to FIG. 8C, the host device may use a timer when determining whether an accessory identifier has been received at block 413A. In this case, if the timer has expired before an accessory identifier has been received, then processing may continue to block 414A, where the host device may switch data pins and then re-send the request.

Figure 8D:
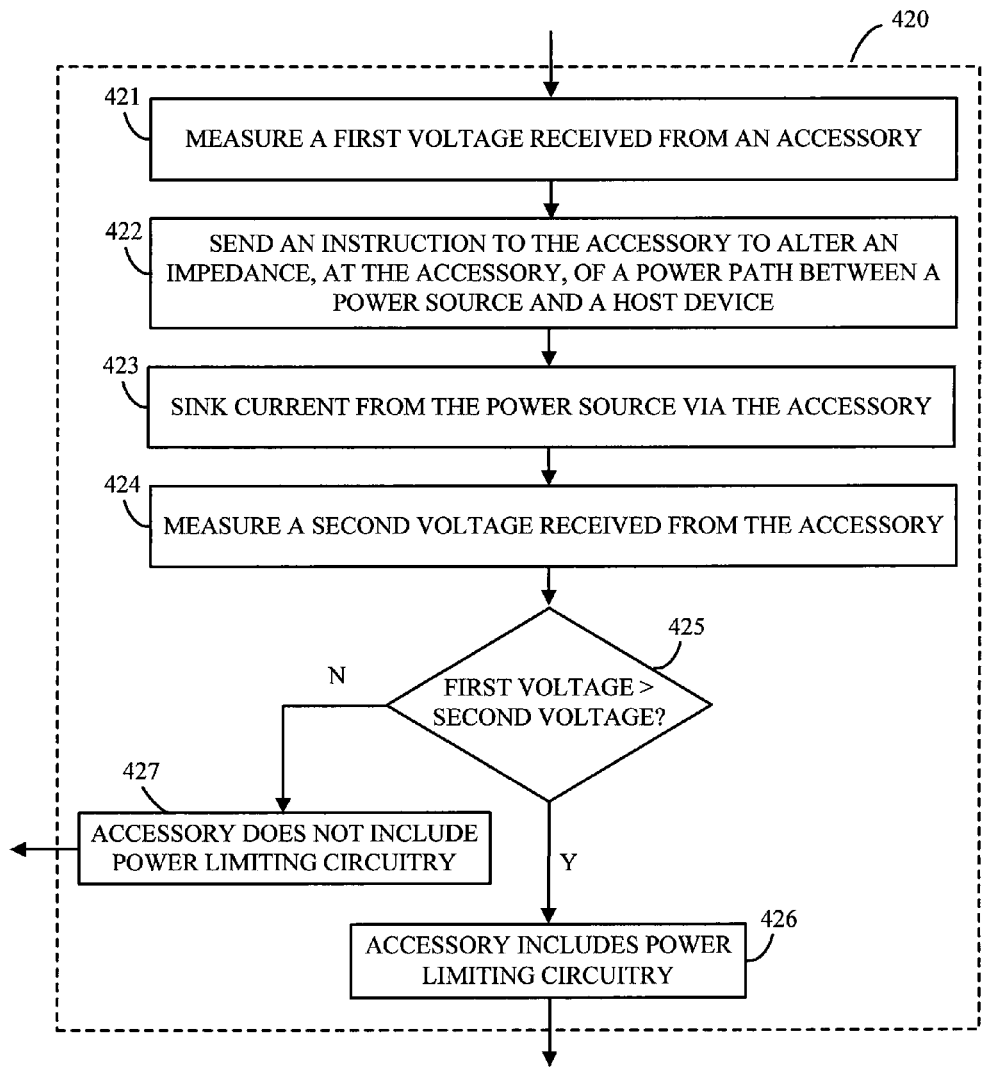
FIG. 8D is a flowchart of a process for determining whether an accessory includes power limiting circuitry according to some embodiments of the present invention.

Turning now to FIG. 8D, FIG. 8D is a flowchart of a process 420 for determining whether an accessory includes particular circuitry (e.g., power limiting circuitry) according to some embodiments of the present invention. Process 420 can be performed by any suitable electronic device such as host device 110 (FIG. 1), but is equally applicable to other electronic devices and accessories described herein. In accordance with some embodiments, process 420 may facilitate or assist in facilitating the establishment or maintenance of a power path between a host device and an accessory. This may include sending instructions from the host device to the accessory, and/or sinking current from the power source via the accessory. Electrical characteristics of the accessory (e.g., a voltage received from the accessory) may be measured before and after such operations are performed, and those electrical characteristics may be compared with one another to determine whether the accessory includes the particular circuitry.

At block 421, a host device (e.g., host device 110 of FIG. 1) measures a first electrical characteristic of an accessory, such as a first voltage received from an accessory (e.g., accessory 120 of FIG. 1). For example, the host device may measure a voltage provided at a power pin of a connector of the host device (e.g., power pin 113). The voltage measured at the power pin may, by way of connection to the accessory, correspond to a voltage provided by a power source (e.g., power source 130) subject to alteration by power limiting circuitry (e.g., power limiting circuitry 121). According to one embodiment, the power limiting circuitry may by default operate in a bypass mode such as that discussed with reference to FIG. 4. Accordingly, the first voltage may be relatively high, such as that shown in the voltage/current characteristic illustrated in FIG. 4.

At block 422, the host device sends an instruction to the accessory to alter an impedance (or other electrical characteristic of the accessory), at the accessory, of a power path between a power source (e.g., power source 130) and a host device (e.g., host device 110). For example, host device 110 may communicate an instruction via data pin 114 to power limiting circuitry 121. The instruction may instruct the power limiting circuitry to switch between modes of operation, such as switching from a bypass mode (such as that discussed with reference to FIG. 4) to a power limiting mode (such as one of those discussed with reference to FIGS. 5A and 5B). In one particular embodiment, the instruction may be communicated to identification circuitry 121*b* which, after determining that the instruction is valid, instructs the impedance altering circuitry 121a to alter the impedance of the power path. To do so, identification circuitry 121b may control third terminal 9 so as to change switch 4 between an ON state and an OFF state. By changing an impedance of power limiting circuitry 121, an impedance of the power path between power source 130 and host device 110 may effectively be altered.

At block 423, the host device sinks current from the power source via the accessory. For example, host device 110 may include a current sink 12 (FIG. 6) coupled to power pin 113, which sinks current from power source 130 via power pin 113 of host device 110, power pin 123 of accessory 120, and power limiting circuitry 121. By sinking current from the power source, the host device may force the power limiting circuitry to operate in a particular mode or in a particular region with reference to its operating characteristics. For example, with reference to FIG. 5B, the host device may draw an amount of current through the power limiting circuitry greater than I_threshold so as to cause the power limiting circuitry to reduce a voltage provided at a power pin (e.g., power pin 123) to approximately 0 V. For another example, with reference to FIG. 5A, the host device may draw an amount of current through the power limiting circuitry greater than I_threshold so as to cause the power limiting circuitry to provide a voltage at a power pin (e.g., power pin 123) that is less than or equal to V_limit.

By both drawing current from the power source via the accessory and sending the instruction to the accessory to alter its impedance, the accessory is effectively forced to operate in a particular operating mode and at a particular operating region. For example, with reference to FIGS. 4, 5A, and 5B, the instruction to enter into a power limiting mode should ensure that the accessory has voltage/current characteristics such as one of those shown in either FIG. 5A or 5B. Then, by forcing an amount of current through the accessory that is at least equal to I_threshold, the voltage output by the accessory should be forced to be approximately V_limit or 0V. Accordingly, by providing such an instruction and forcing such an amount of current through the accessory, the host device can determine whether the accessory includes not only the circuitry necessary to interpret the instruction sent from the host device but also the circuitry necessary to change an impedance of the power path between the power source and the host device.

At block 424, the host device measures a second voltage received from the accessory. The second voltage measurement may be made in a manner similar to that of the first voltage measurement. For example, host device 110 may again measure a voltage provided at power pin 113.

At block 425, the host device determines whether the accessory includes the particular circuitry (e.g., power limiting circuitry 121) based on the relationship between the first voltage (or other electrical characteristic) measured at block 421 and the second voltage (or other electrical characteristic) measured at block 424. In one embodiment, the host device does this by determining whether the first voltage is greater than the second voltage. If it is determined that the first voltage is greater than the second voltage, then processing continues to block 426 where the host device determines that the accessory includes the particular circuitry. If it is determined that the first voltage is not greater than the second voltage, then processing continues to block 427 where the host device determines that the accessory does not include the particular circuitry.

For example, with reference to FIG. 4, the first voltage may be measured while power limiting circuitry 121 operates in bypass mode and is thus relatively high. Turning to FIGS. 5A and 5B, the second voltage may then be measured to be relatively low as long as an amount of current equal to or greater than I_threshold is drawn through power limiting circuitry 121. By measuring a difference in voltage, and/or by determining that the second voltage is approximately equal to some value (e.g., V_limit or 0V), host device 110 may determine that accessory 120 includes power limiting circuitry 121. In some embodiments, block 423, that is the sinking of current by the host device from the power source, may ensure that at least an amount of current equal to I_threshold is drawn through the power limiting circuitry. In other embodiments, such a current sink may be excluded as the power source may provide such current in any event.

It should be apparent that accessories without power limiting circuitry may not change an electrical characteristic in response to one or more of the operations performed at blocks 422 and 423. For example, an accessory that does not include power limiting circuitry may pass power from the power source to the host device unaltered, as shown in FIG. 4. In such cases, both a first and second measured voltage would be approximately the same, and thus the host device may determine that the accessory does not include the power limiting circuitry.

It should also be recognized that embodiments of the invention are not limited to measuring and comparing voltages received from an accessory. Rather, other electrical characteristics of the accessory and/or a power path between a power source and a host device via the accessory may be measured and compared. For example, the host device may measure and compare impedances, voltages, currents, voltage/current magnitudes, voltage/current phases, etc.

Further, one of ordinary skill would recognize that embodiments may not be limited to determining whether the first voltage is greater than the second voltage as discussed with reference to block 425, but in some cases at block 425 the host device may alternatively determine whether the first voltage is less than the second voltage and, if so, conclude that the accessory includes power limiting circuitry. For example, prior to measuring the first voltage, current may be sinked from the power source. Then, after measuring the first voltage, the current sink may be removed, and the second voltage measured thereafter. For another example, at block 422, instead of instructing the accessory to switch from a bypass mode to a power limiting mode, the host device may instruct the accessory to switch from a power limiting mode to a bypass mode.

It should be appreciated that the specific operations illustrated in FIGS. 8A to 8D provide particular methods that may be executed by a host device, according to certain embodiments of the present invention. While the operations illustrated in FIGS. 8A to 8D are often discussed with reference to FIG. 1, it should be appreciated that the operations may be performed by other types of host devices and accessories. Further, other sequences of operations may also be performed according to alternative embodiments. For example, alternative embodiments of the present invention may perform the operations outlined above in a different order. Moreover, the individual operations illustrated in FIGS. 8A to 8D may include multiple sub-operations that may be performed in various sequences as appropriate to the individual operations.

Further, additional operations may be added depending on the particular applications. For example, before block 421 of measuring a first voltage received from the accessory, the host device may communicate an instruction to the accessory to operate in a particular mode of operation, such as a bypass mode. Moreover, existing operations may be removed depending on the particular applications. For example, block 422 or block 423 may be omitted. Where block 422 is omitted, the current sink may force the power limiting circuitry to operate in different regions of a mode of operation, where the different regions have measurable differences in electrical characteristics. Where block 423 is omitted, the instruction from the host device to the accessory may cause the power limiting circuitry to operate in different modes of operation having measurable differences in electrical characteristics. Further, one of ordinary skill in the art would readily recognize that the power limiting circuitry may operate to alter not only a voltage provided at a power pin (e.g., power pin 123) as discussed above, but could similarly alter other electrical characteristics of the accessory and/or the power path provided between the power source and the host device.

As mentioned, various functionality of the host device may be implemented in hardware, software, or a combination thereof. In one particular embodiment, the functionality of the host device that operates the processes depicted in and discussed with reference to FIGS. 8B and 8C may be implemented in hardware, whereas that of FIG. 8D may be implemented in software. In such an embodiment, the hardware circuitry that performs the operations discussed with reference to FIGS. 8B and 8C may be operable to execute using no or only a very small amount of power. As a result of these operations being performed, the host device may then, at least temporarily, receive power from the accessory. Once the host device begins to receive full operating power via the accessory, the host device may boot up its operating system, and subsequently perform the operations discussed with reference to FIG. 8D for determining whether or not to continue receiving power via the accessory.

Figure 9A:
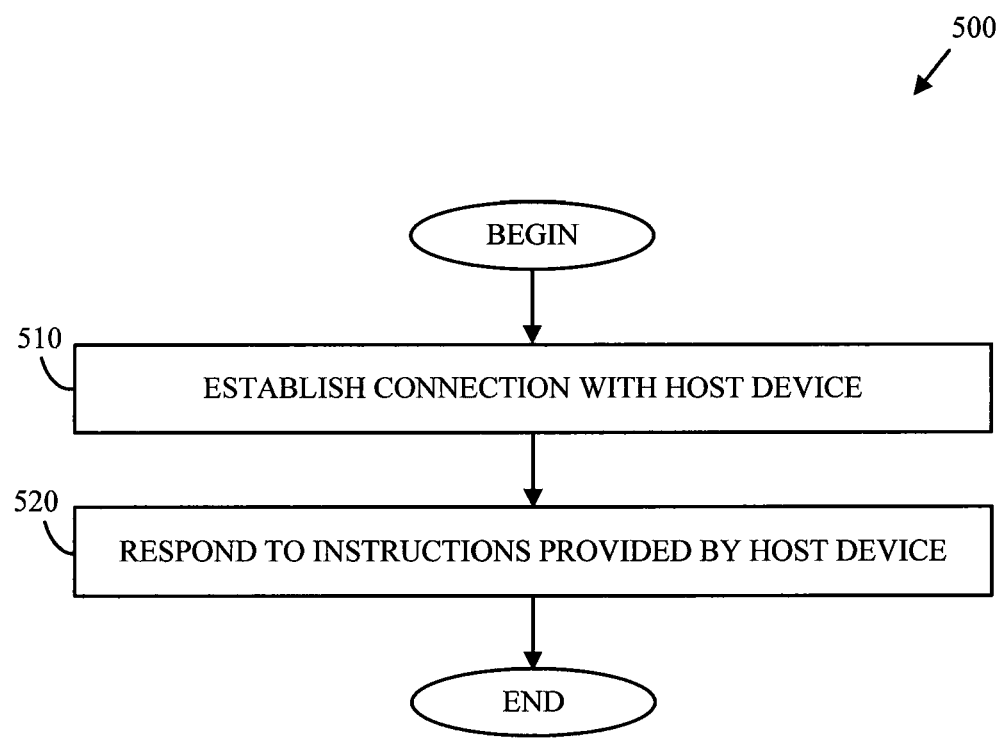
FIG. 9A is a flowchart of a process for operating an accessory according to an embodiment of the present invention.

FIG. 9A is a flowchart of a process 500 for operating an accessory, such as accessory 120, according to an embodiment of the present invention. Process 500 can be performed by any suitable electronic device such as accessory 120 (FIG. 1), but is equally applicable to other accessories described herein.

At block 510, the accessory (e.g., accessory 120) establishes a connection with a host device (e.g., host device 110). In establishing a connection with the host device, the accessory and the host device may engage in a handshaking protocol so as to facilitate communication between the devices. In some embodiments, establishing a connection may include the accessory receiving power from the host device, and in some cases, may also or alternatively include the accessory communicating power to the host device from a power source. Some particular embodiments for establishing a connection with a host device are discussed with reference to FIG. 9B.

At block 520, the accessory (e.g., accessory 120) responds to instructions provided by the host device (e.g., host device 110). In responding to instructions, the accessory may communicate information back to the host device and/or, in some embodiments, may alter a power path between a power source and the host device. Some particular embodiments for responding to instructions provided by the host device are discussed with reference to FIG. 9C.

Figure 9B:
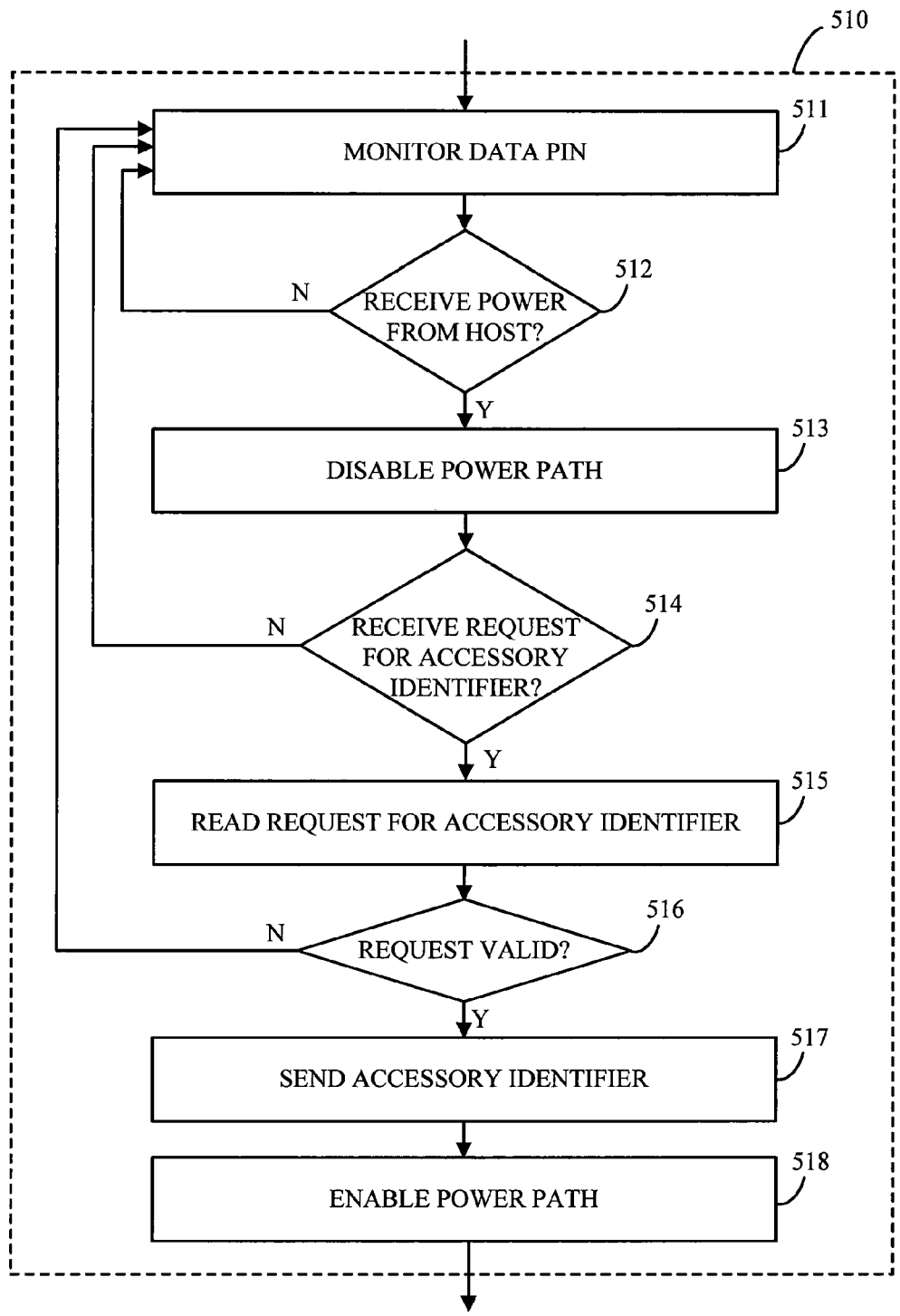
FIG. 9B is a flowchart of a process for an accessory to establish a connection with a host device according to some embodiments of the present invention.

Turning now to FIG. 9B, FIG. 9B is a flowchart of a process for an accessory (e.g., accessory 120) to establish a connection with a host device (e.g., host device 110) according to some embodiments of the present invention. At block 511, the accessory monitors a data pin of the accessory. For example, with reference to FIG. 1, accessory 120 may monitor data pin 124. Monitoring may be performed by a processor or other circuitry and/or software in the accessory, such as by power limiting circuitry 121. In monitoring the data pin, the accessory may monitor the data pin for information received from the host device, such as a power signal and/or a request for an accessory identifier. For example, in one embodiment, identification circuitry 121b (FIG. 2) may monitor data pin 124 for changes in logic levels.

At block 512, the accessory determines whether it received power from the host device. In some embodiments, the accessory may receive power from the host device. The accessory may receive any suitable amount of power, such as an amount of power sufficient for the accessory to operate at least for a certain period of time. The power may be communicated from the host device to the accessory using one or more techniques. For example, the host device may wirelessly communicate power to the accessory using electromagnetic induction, electromagnetic radiation, electrical conduction, etc. In some embodiments, the power may be communicated from the host device to the accessory by wire. For example, with reference to FIG. 1, host device 110 may communicate power to accessory 120 via a pin of connector 122. The line which the host device communicates power to the accessory may be the same or different than a line which the host device uses to communicate information to the accessory. For example, with reference to FIG. 1, host device 110 may communicate both power and information to accessory via data pin 114. For another example, host device 110 may communicate information to accessory 120 via data pin 114, and power to accessory 120 via a pin other than data pin 114. In at least one embodiment, host device 110 may communicate power to accessory 120 by maintaining the voltage at a data pin at a high state. Upon connecting host device 110 to accessory 120, identification circuitry 121b or other internal circuitry may then determine that power is received from the host by identifying a high voltage level at data pin 124.

In the event the accessory does not detect any received power from the host device, the accessory may continue to monitor the data pin as discussed with reference to block 511. In contrast, in the event the accessory detects power received from the host device, processing may continue with block 513.

At block 513, the accessory disables a power path between a power source and the host device. For example, with reference to FIG. 1, accessory 120 may disable a power path from power source 130 to host device 110. The accessory may disable the power path using one or more of a variety of techniques. In one embodiment, the accessory may increase an impedance of the power path between the power source and the host device. For example, with reference to FIG. 1, power limiting circuitry 121 may increase an impedance of the power path between power source 130 and host device 110.

In some embodiments, power limiting circuitry 121 includes identification circuitry 121b and impedance altering circuitry 121a as discussed with reference to FIG. 3, where the impedance altering circuitry 121a may be operable in a bypass mode and a power limiting mode, as previously described. To disable the power path, identification circuitry 121b may communicate an instruction to impedance altering circuitry 121a to switch from the bypass mode to the power limiting mode.

At block 514, the accessory determines whether a request for an accessory identifier is received. For example, with reference to FIG. 1, power limiting circuitry 121 may determine whether a request for an accessory identifier is received via data pin 114. If the accessory determines that a request for an accessory identifier is not received, processing may continue with block 511, where the accessory continues to monitor the data pin. If, on the other hand, the accessory determines that a request for an accessory identifier is received, processing may continue with block 515.

At block 515, the accessory reads the request for an accessory identifier. For example, with reference to FIG. 1, power limiting circuitry 121 may read the request for an accessory identifier on data pin 124. In some embodiments, the received request may be stored by the accessory.

At block 516, the accessory determines whether the request for an accessory identifier is valid. Determining the validity of the received request may include one or more of a variety of operations. In one embodiment, the request for an accessory identifier may be communicated using one or more of a variety of error detection and, in some embodiments, error correction, techniques, as described above with respect to FIG. 8C. Accordingly, determining the validity of the received request may include performing error detection on the request. In some embodiments, this may include using error detection information, such as parity bits, checksums, CRC check values, hash function outputs, etc., communicated with or separate from the request. In the event the accessory does not detect any errors in the received request, the accessory may determine that the received request is valid. In contrast, in the event the accessory detects one or more errors in the received request, the accessory may determine that the received request is not valid. In some embodiments, in the event the accessory detects one or more errors in the received request, the accessory may attempt to correct those errors and subsequently determine that the received request is not valid only if it is unable to correct at least one of those errors.

In another embodiment, at least portions of the received request for an accessory identifier may be compared to a list of authorized host identifiers. For example, the request for an accessory identifier may include a host identifier as previously described with reference to FIG. 8C. The accessory may have stored therein, or be operable to access from a location remote from the accessory, a database including the list of authorized host identifiers, where the host identifiers provided on the list have been authorized to operate with the accessory. By comparing the received host identifier included in the request (or in some embodiments, received separate from the request) to the list of authorized host identifiers, the accessory may check to see if the received host identifier matches one or more of the host identifiers provided on the list. In the event of a match, the accessory may determine that the received request for an accessory identifier is valid. In contrast, in the event the received host identifier does not match any of the host identifiers provided on the list, the accessory may determine that the received request for an accessory identifier is not valid.

If the accessory determines that the received request is not valid, processing may continue with block 511, where the accessory operates to monitor the data pin. In contrast, if the accessory determines that the received request is valid, processing may continue with block 517.

At block 517, the accessory sends its accessory identifier to the host device. For example, with reference to FIG. 1, accessory 120 may send the accessory identifier to host device 110 via data pin 124. In some embodiments, the accessory identifier may be stored in accessory 120. In other embodiments, the accessory identifier may be acquired by accessory 120 from a source remote from accessory 120.

At block 518, the accessory enables a power path between the power source and the host device. For example, with reference to FIG. 1, accessory 120 enables the power path from power source 130 to host device 110. The accessory may enable the power path using one or more of a variety of techniques. In one embodiment, the accessory may decrease an impedance of the power path between the power source and the host device. For example, with reference to FIG. 1, power limiting circuitry 121 may decrease an impedance of the power path between power source 130 and host device 110.

In some embodiments, power limiting circuitry 121 includes identification circuitry 121b and impedance altering circuitry 121a as discussed with reference to FIG. 2, where the impedance altering circuitry 121a may have be operable in a bypass mode and a power limiting mode, as previously described. To enable the power path, identification circuitry 121b may communicate an instruction to impedance altering circuitry 121a to switch from the power limiting mode to the bypass mode.

The accessory enabling a power path at block 518 should be distinguished from the host receiving power at block 417 (FIG. 8B) and receiving power as performing action "A" at block 430 (FIG. 8A). The accessory may provide a voltage at a power pin of the host device, however whether that voltage is consumed or otherwise used by the host device is a different matter. The accessory enabling a power path refers to whether the accessory allows a voltage provided by a power source to pass through to the host device substantially unaltered, or whether the accessory suppresses, reduces, or otherwise alters that voltage. In contrast, regardless of whether the accessory actually enables such a power path, the host device may decide whether or not to accept or otherwise consume power supplied to a power pin (or other pin). At block 417, the host device may receive the power at least temporarily, for example to charge the host device or provide the host device with sufficient power to operate in the event the host device does not otherwise have access to power sufficient to operate (e.g., it has a dead battery). The host devices determination to receive supplied power may then change based on a subsequent determination of whether the accessory includes power limiting circuitry. If it does include such circuitry, the host device may then continue to receive the supplied power. Otherwise, it may then refuse to receive the supplied power.

Figure 9C:
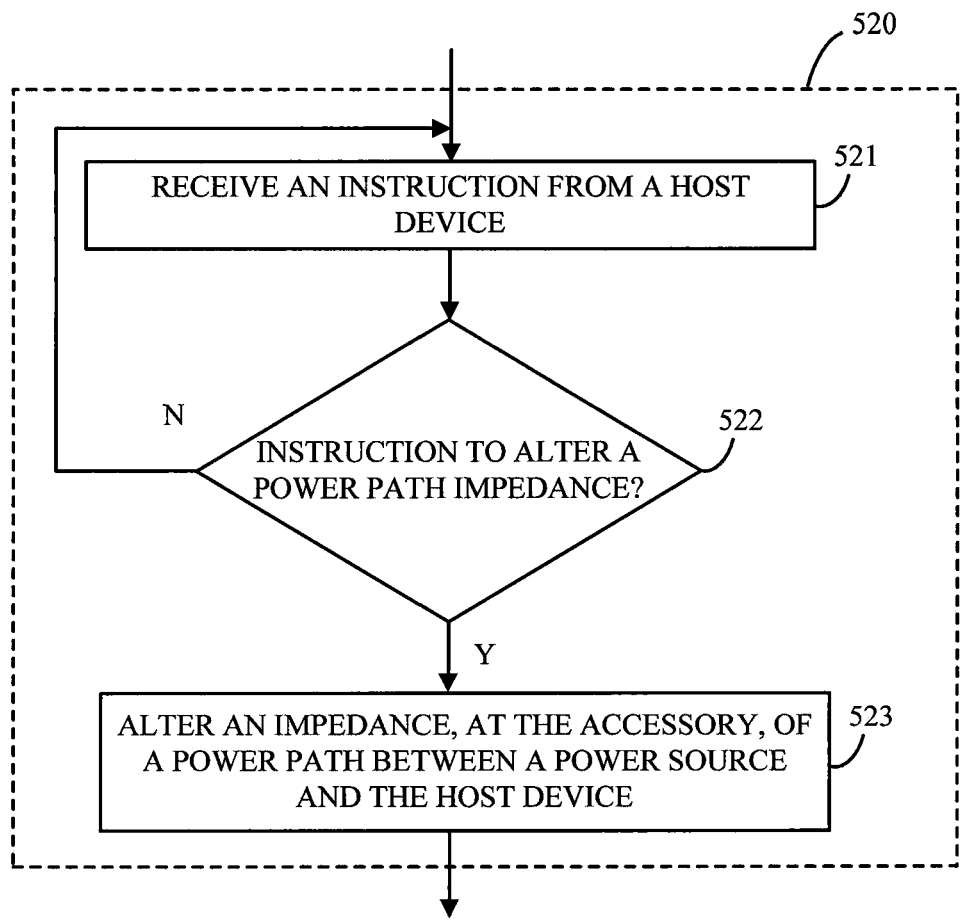
FIG. 9C is a flowchart of a process for an accessory to respond to instructions provided by a host device according to some embodiments of the present invention.

Turning now to FIG. 9C, FIG. 9C is a flowchart of a process 520 for an accessory to respond to instructions provided by a host device according to some embodiments of the present invention. Process 520 can be performed by any suitable electronic device such as accessory 120 (FIG. 1), but is equally applicable to other electronic devices and accessories described herein. In accordance with some embodiments, process 520 may facilitate or assist in facilitating the establishment of a power path between a host device and an accessory. This may include receiving instructions from the host device and responding to those instructions by altering an impedance of a power path between a power source and the host device.

At block 521, the accessory (e.g., accessory 120) receives an instruction from the host device (e.g., host device 110). For example, the power limiting circuitry (e.g., power limiting circuitry 121) in the accessory may receive an instruction communicated from the host device via one or more data pins (e.g., data pin 114 and data pin 124). The instruction may be communicated using any suitable communication protocol.

At block 522, the accessory determines whether the instruction is an instruction to alter a power path impedance, such as an impedance of a power path between the power source and the host device. If it is determined that the instruction is not an instruction to alter a power path impedance, processing may return to the beginning of operations so that the accessory waits to receive another instruction from the host device. If it is determined that the instruction is an instruction to alter a power path impedance, processing may continue with block 523.

In one embodiment and with reference to FIG. 3, the instruction may be an instruction to cause switch 4 to enter into either an ON state or an OFF state. For example, the instruction may cause switch 4 to enter into an OFF state so that impedance altering circuitry 121a (FIG. 2) has a voltage/current characteristic similar to that discussed with reference to FIG. 5A. Alternatively, the instruction may cause switch 4 to enter into an ON state so that impedance altering circuitry 121a has a voltage/current characteristic similar to that discussed with reference to FIG. 4.

At block 523, the power limiting circuitry alters an impedance, at the accessory, of a power path between the power source and the host device. For example, with reference to FIG. 5B, in response to receiving an instruction to enter a power limiting mode, accessory 120 may alter its impedance such that a voltage provided at power pin 123 is approximately 0V when at least a threshold amount of current (I_threshold) is drawn through impedance altering circuitry 121a. In another example, with reference to FIG. 5A, in response to receiving an instruction to enter a power limiting mode, accessory 120 may alter its impedance such that a voltage provided at power pin 123 is decreased compared to a voltage provided by power source 130 with an increasing an amount of current. In yet another example, in response to receiving an instruction to enter into a bypass mode, accessory 120 may alter its impedance such that a voltage provided by power source 130 is approximately equal to a voltage provided at power pin 123 for any given current such as that depicted in FIG. 4.

It should be appreciated that the specific operations illustrated in FIGS. 9A to 9C provide particular methods that may be executed by an accessory, according to certain embodiments of the present invention. While the operations illustrated in FIGS. 9A to 9C are often discussed with reference to FIG. 1, it should be appreciated that the operations may be performed by other host devices and accessories described herein. Further, other sequences of operations may also be performed according to alternative embodiments. For example, alternative embodiments of the present invention may perform the operations outlined above in a different order. Moreover, the individual operations illustrated in FIGS. 9A to 9C may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives. For example, one of ordinary skill in the art would readily recognize that power limiting circuitry 121 may operate to alter not only an impedance of a power path as discussed above, but could similarly alter other electrical characteristics of accessory 120 and/or the power path provided between power source 130 and host device 110.

Figure 10A:
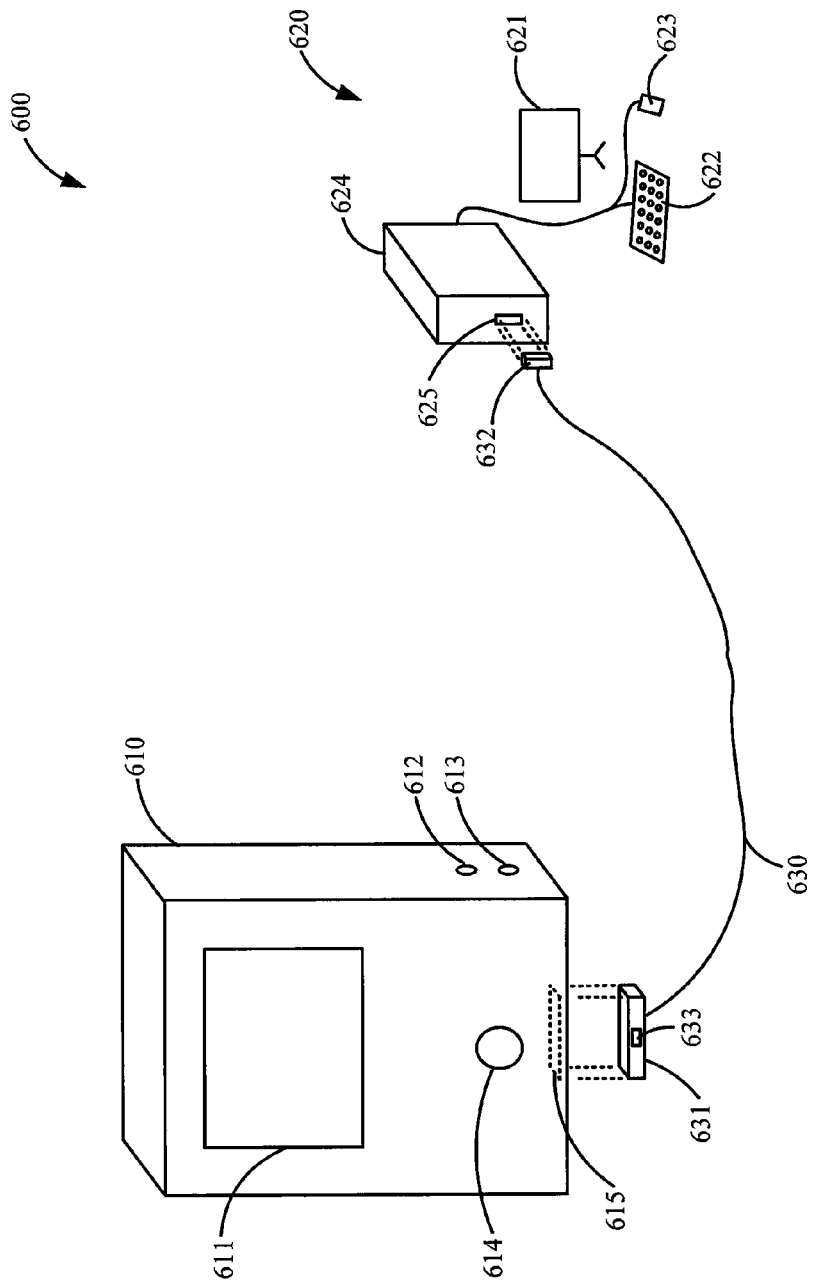
FIG. 10A illustrates a system for determining whether an accessory includes particular circuitry according to a first embodiment of the present invention.

FIG. 10A a system 600 for determining whether an accessory includes particular circuitry according to a first embodiment of the present invention. According to this embodiment, system 600 includes a host device 610 (e.g., host device 110 of FIG. 1), a computing system 620 (e.g., power source 130 of FIG. 1), and an accessory 630 (e.g., accessory 120 of FIG. 1). Host device 610 is electrically coupleable to computing system 620 via accessory 630.

Host device 610 may be any suitable electronic device that is operable to determine whether accessory 630 includes particular circuitry, and may include one or more hardware and or software components operable to facilitate determining whether accessory 630 includes particular circuitry. For example, host device 610 may be a mobile phone, a personal digital assistant (PDA), a handheld or portable device (e.g., iPhone™, Blackberry™, etc.), a notebook, a personal computer, a note pad, a tablet computer, a media player (e.g., a music player or video player), a camera, a game player, a laptop computer, a netbook, a booklet, or other electronic device configured for wired or wireless communication. Host device 610 may include any suitable components typically found in such electronic devices necessary to perform the operations discussed herein. For example, host device 610 may include a user interface 611 that may be operable to display information to the user or receive inputs from the user (e.g., a touchscreen), a speaker 612 for providing an audio output to a user, a microphone 613 for receiving audio inputs from a user, one or more buttons 614 for controlling the operation of host device 610 via a user input, a connector 615 such as a plug connector or a receptacle connector for mechanically and electrically coupling host device 610 to other electronic components such as accessory 630, where connector 615 may include one or more pins or conductive contacts for establishing electrical and/or optical communication with corresponding pins or contacts of a connector coupled to connector 615. Host device 610 may also include other suitable components typically found in such systems for performing the operations discussed herein, such as a processor (not shown), a tangible non-transitory computer readable storage medium (not shown), and the like, all operably coupled to one another such that the processor may execute instructions stored on the computer readable storage medium so as to cause host device 610 to perform one or more of the operations discussed herein.

Accessory 630 may be any suitable electronic element operable to establish a power path between host device 610 and a power source (such as one provided in computing system 620, one provided via a power socket in a wall, one provided as a battery, etc.), and/or operable to establish a communication path between host device 610 and another electronic computing device such as computing system 620.

Accessory 630 according to this embodiment is a cable that includes one or more conductive wires disposed therein, where the wires may be individually insulated and, in some embodiments, the group of conductive wires may be bundled by an insulating sheath. The wires of accessory 630 may be operable to carry voltage and current between host device 610 and other devices and/or power supplies, such as computing system 620. In some embodiments, accessory 630 may additionally or alternatively include optical conductors such as optical fibers operable to communicate light or other electromagnetic waves between host device 610 and computing system 620.

Accessory 630 may include a first connector 631 which may be any suitable connector, such as a plug connector or a receptacle connector, that includes one or more pins or conductive contacts for mechanically, electrically, and/or optically coupling the wires and/or optical conductors of accessory 630 to host device 610 so as to establish a power path and/or a communication path between host device 610 and other devices and/or power sources, such as computing system 620. For example, first connector 631 may be a 30-pin connector such as that described in U.S. Pat. No. 6,776,660, which is incorporated herein by reference in its entirety for all purposes, a dual-orientation connector such as any of those described in U.S. Provisional Patent Application No. 61/556,692, filed Nov. 7, 2011, U.S. Provisional Patent Application No. 61/565,372, filed Nov. 30, 2011, U.S. Patent Application No. 61/694,423, titled "DUAL ORIENTATION ELECTRONIC CONNECTOR", filed Aug. 29, 2012 and U.S. patent application Ser. No. 14/357,200, titled "CONNECTORS FOR ELECTRONIC DEVICES", filed sep. 7, 2012, all of which are incorporated herein by reference in their entirety for all purposes, an RS232 serial connector, a USB connector, an S-video connector, a VGA connector, an SDI connector, etc. First connector 631 may be sized and shaped to mechanically engage with connector 615 of host device 610, and connector 615 of host device 610 may be sized and shaped to mechanically engage with first connector 631.

Accessory 630 may also include a second connector 632 which may be any suitable connector, such as a plug connector or a receptacle connector, that includes one or more pins or conductive contacts for mechanically, electrically, and/or optically coupling the wires and/or optical conductors of accessory 630 to computing system 620 so as to establish a power path and/or a communication path between computing system 620 and host device 610. For example, second connector 632 may be a 30-pin connector such as that described in U.S. Pat. No. 6,776,660, a dual-orientation connector such as any of those described in U.S. Provisional Patent Application No. 61/556,692, filed Nov. 7, 2011, U.S. Provisional Patent Application No. 61/565,372, filed Nov. 30, 2011, U.S. Patent Application No. 61/694,423, titled "DUAL ORIENTATION ELECTRONIC CONNECTOR", filed Aug. 29, 2012, and U.S. patent application Ser. No. 14/357,200, titled "CONNECTORS FOR ELECTRONIC DEVICES", filed sep. 7, 2012, all of which are incorporated herein by reference in their entirety for all purposes, an RS232 serial connector, a USB connector, an S-video connector, a VGA connector, an SDI connector, etc. Second connector 632 may be the same or different than first connector 631.

Accessory 630 may further include power path control circuitry 633 (e.g., power limiting circuitry 121) which may be any suitable hardware and/or software for controlling a power path and/or communication path between first connector 631 and second connector 632.

Since power path control circuitry 633 is operable to control a power path and/or communication path between first connector 631 and second connector 632, power path control circuitry 633 may also be operable to control a power path and/or communication path between devices that may be mechanically, electrically, and/or optically coupled to the connectors of accessory 630, such as host device 610 and computing system 620. Power path control circuitry 633 may control the power path between host device 610 and computing system 620 in any one or more of a number of fashions. For example, power path control circuitry 633 may be operable to selectively alter a characteristic of the power path, such as an electrical impedance, a voltage capacity, a current capacity, and the like of accessory 630. Additionally or alternatively, power path control circuitry 633 may impose power limits, voltage limits, and/or current limits on power, voltage, and/or current, respectively, supplied from computing system 620. In some embodiments, power path control circuitry 633 may impose limits on amplitude, frequency, phase, and/or other characteristics of a signal, such as an electrical signal and/or an optical signal, communicated from computing system 620.

As shown in FIG. 10A, power path control circuitry 633 may be provided entirely as part of first connector 631. However, the location of power path control circuitry 633 is not so limited. For example, in some embodiments, power path control circuitry 633 may be located entirely between first connector 631 and second connector 632, entirely within second connector 632, or have portions that are located in one or more of first connector 631, second connector 632, and between first connector 631 and second connector 632.

Computing system 620 may be any suitable electronic component(s) for providing power to and/or communicating with host device 610 via accessory 630. In one embodiment, computing system 620 includes various components for both providing power to host device 610 and establishing communications with host device 610. For example, computing system 620 may include a display 621 for displaying information to a user, a user interface for receiving inputs from the user including a keyboard 622 and a mouse 623, and a housing 624 that is configured to house various electronic components for enabling computing system 620 to provide power to and/or communicate with host device 610. In some embodiments, housing 624 may include a processor (not shown), a tangible non-transitory computer readable storage medium (not shown), and the like, all operably coupled to one another such that the processor may execute instructions stored on the computer readable storage medium so as to cause computing system 620 to perform one or more of the operations discussed herein. Housing 624 may also include a connector 625 such as a plug connector or a receptacle connector for mechanically and electrically coupling computing system 620 to other electronic components such as host device 610. In some embodiments, connector 625 may include one or more pins or conductive contacts for establishing electrical and/or optical communication with corresponding pins or contacts of a second connector 632 of accessory 630. Connector 625 may be sized and shaped to mechanically engage with second connector 632 of accessory 630, and second connector 632 may be sized and shaped to mechanically engage with connector 625.

Computing system 620 may include a power source such as a battery (not shown) for providing power to host device 610 via a power path established between the power source and connector 625. In some embodiments, computing system 620 may receive power from a power source external to computing system 620, such as from an external battery, power generator, and/or wall socket/electrical outlet. In some embodiments, computing system 620 may include power conversion circuitry (not shown) for converting AC power supplied from an external source to DC power consumed by computing system 620 and/or communicated to host device 610 via connector 625.

It should be recognized that embodiments are not limited to requiring host device 610 to be coupled to a computing system 620. Rather, in some embodiments, host device 610 may be coupled to any suitable electronic component via accessory 630 so as to establish a power path and/or communication path between host device 610 and a power source. For example, instead of being coupled to computing system 620, host device 610 may be coupled to a power source via an electrical socket such as those provided in a wall, to a battery, to an AC/DC converter which itself is coupled to an electrical socket, etc.

Figure 10B:
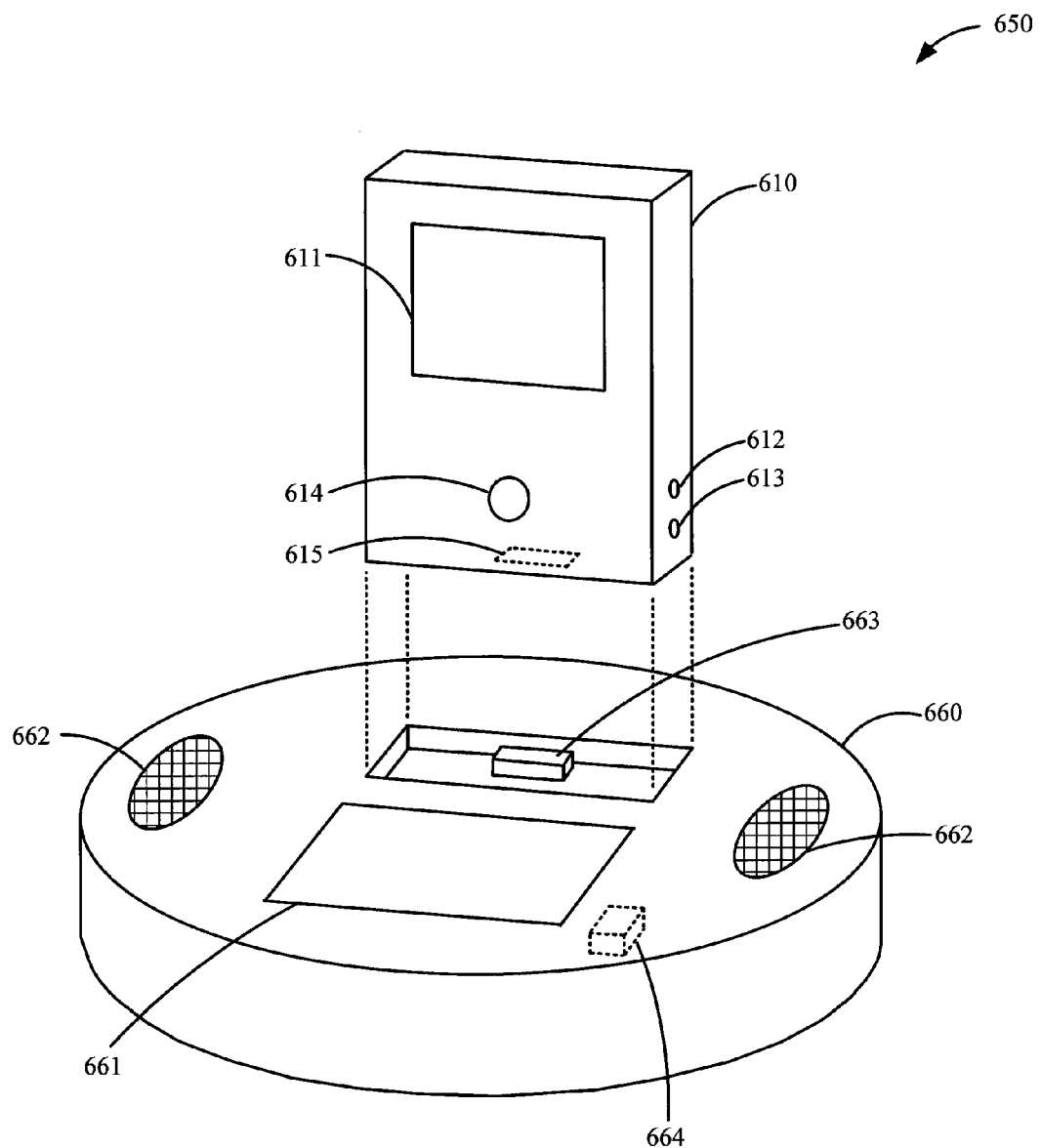
FIG. 10B illustrates a system for determining whether an accessory includes particular circuitry according to a second embodiment of the present invention.

FIG. 10B illustrates a system 650 for determining whether an accessory includes particular circuitry according to a second embodiment of the present invention. In this embodiment, system 650 includes host device 610 as discussed with reference to FIG. 10A, and accessory 660. Host device 610 may be electrically and mechanically coupleable to accessory 660.

Accessory 660, like accessory 630, may be any suitable electronic device operable to establish a power path between host device 610 and a power source (such as one provided in accessory 660, and/or one provided external to accessory 660 but to which accessory 660 is electrically coupled), and/or operable to establish a communication path between host device 610 and electronic components (such as electronic components of accessory 660 and/or electronic components external to accessory 660). For example, accessory 660 may be an alarm clock, a radio, a speaker set, a docking station, an input device such as a keyboard, a musical instrument such as a digital piano, a battery, a charging station, an image/video projection unit, etc. Accessory 660 may include components typically found in such electronic devices for performing the operations discussed herein. For example, accessory 660 may include a user interface 661 that may be operable to display information (e.g., a current time) to a user and/or receive information (e.g., via a touchscreen), speakers 662 for providing an audio output to a user, a connector 663 (e.g., a receptacle connector or a plug connector) for mechanically, electrically, and/or optically coupling accessory 660 to other electronic components such as host device 610, etc., where connector 663 may include one or more pins or conductive contacts for establishing electrical and/or optical communication with corresponding pins or contacts of a connector coupled to receptacle connector 663, such as connector 615 of host device 610.

Accessory 660 may include a power source such as a battery (not shown) for providing power to host device 610 via a power path established between the power source and connector 615. In some embodiments, accessory 660 may also or alternatively receive power from a power source external to accessory 660, such as from an external battery, power generator, and/or wall socket/electrical outlet. In at least one embodiment, accessory 660 may also include power conversion circuitry (not shown) for converting AC power supplied from an external source to DC power consumed by accessory 660 and/or communicated to host device 610 via connector 663.

Accessory 660 may also include power path control circuitry 664 which may be any suitable hardware and/or software for controlling a power path and/or communication path between a power source and connector 663. Since power path control circuitry 664 is operable to control a power path and/or communication path between a power source and receptacle connector 663, power path control circuitry 664 may also be operable to control a power path and/or communication path between devices that may be mechanically, electrically, and/or optically coupled to receptacle connector 663 of accessory 660, such as host device 610. Power path control circuitry 664 may control the power path between the power source and host device 610 in any one or more of a number of fashions. In one embodiment, power path control circuitry 664 may operate similar to power path control circuitry 633. For example, power path control circuitry 664 may be operable to alter a characteristic of the power path, such as electrical impedance, voltage capacity, current capacity, and the like of accessory 660. Additionally or alternatively, power path control circuitry 664 may impose power limits, voltage limits, and/or current limits on power, voltage, and/or current supplied from the power source and/or other components of accessory 660. In some embodiments, power path control circuitry 664 may impose limits on amplitude, frequency, phase, and/or other characteristics of a signal, such as an electrical signal and/or an optical signal, communicated from the power source and/or other components of accessory 660.

Systems 600 and 650 in certain embodiments are systems for determining whether an accessory includes particular circuitry such as power limiting circuitry. However, it will be appreciated by those of ordinary skill in the art that such systems could operate equally well with fewer or a greater number of components than are illustrated in FIGS. 10A and 10B. Further, those of ordinary skill in the art would recognize that the systems could operate equally well where the components of the systems, such as host device 610 and accessory 630/660, have fewer or a greater number of components than are illustrated in FIGS. 10A and 10B. Thus, the depiction of systems 600 and 650 in FIGS. 10A and 10B should be taken as being illustrative in nature, and not limiting to the scope of the disclosure.

Figure 11A:
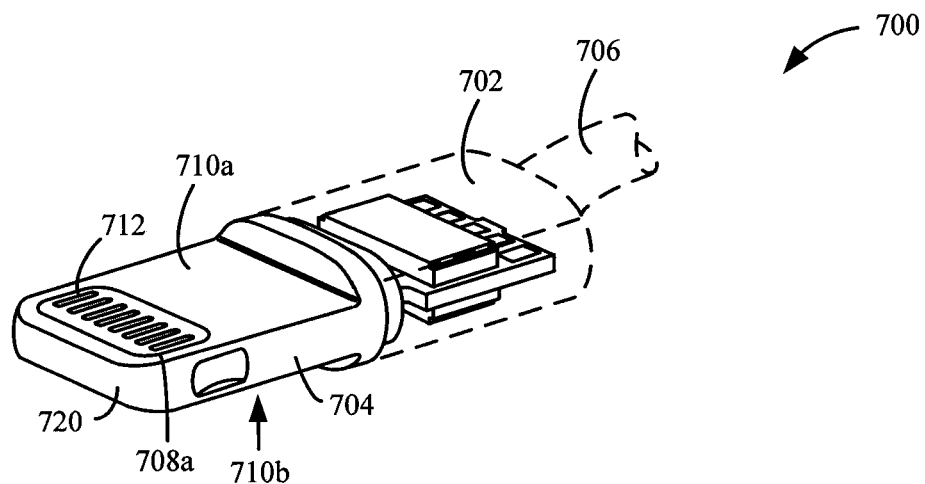
FIG. 11A illustrates a plug connector according to an embodiment of the present invention.

FIG. 11A illustrates a plug connector 700 according to an embodiment of the present invention. Plug connector 700 is an example of a plug connector used herein to explain various embodiments of the present invention. Plug connector 700 may correspond, for example, to connector 112 and/or connector 122 (FIG. 1), and may be operatively mated to a corresponding receptacle connector in either of two orientations 180 degrees rotated from each other. One skilled in the art will realize that many other forms and types of connectors other than plug connector 700 can be used and that techniques described herein will apply to any plug connector that has the characteristics of plug connector 100.

Plug connector 700 includes a body 702 and a tab portion 704. A cable 706 is attached to body 702 and tab portion 704 and extends away from body 702 in a direction parallel to the length of the connector 700. Tab 704 is sized to be inserted into a corresponding receptacle connector during a mating event and includes a first contact region 708*a* formed on a first major surface 710*a* and a second contact region 708C (not shown in FIG. 11A) formed at a second major surface 710*b* opposite surface 710*a*. A plurality of contacts 712 can be formed in each of contact regions 708*a* and 708C such that, when tab 704 is inserted into a corresponding receptacle connector, contacts 712 in regions 708*a* and/or 708C are electrically coupled to corresponding contacts in the receptacle connector. In some embodiments, contacts 712 are self-cleaning wiping contacts that, after initially coming into contact with a receptacle connector contact during a mating event, slide further past the receptacle connector contact with a wiping motion before reaching a final, desired contact position.

Figure 11B:
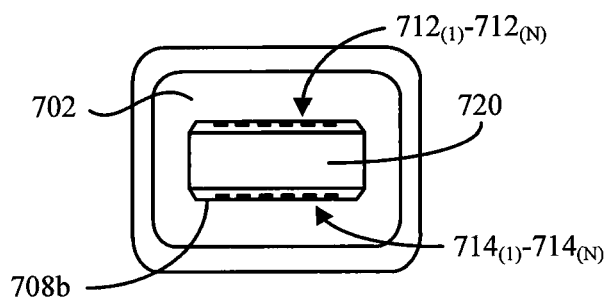
FIG. 11B is a simplified, cross-sectional view of the plug connector according to an embodiment of the present invention.

FIG. 11B illustrates a simplified, cross-sectional view of plug connector 700. The front view illustrates a cap 720. Cap 720 can be made from a metal or other conductive material and can extend from the distal tip of connector 700 along the side of the connector towards body 702 either fully or partially surrounding contacts 712 formed in contact regions 708*a* and 708C in the X and Y directions. In some embodiments, cap 720 can be grounded in order to minimize interference that may otherwise occur on contacts 712 of connector 700 and can thus be referred to as a ground ring. Contacts $712_{(1)}$-$712_{(N)}$ can be positioned within contact region 708*a* and additional contacts $714_{(1)}$-$714_{(N)}$ can be positioned within region 708C on the opposing surface of tab 704. In some embodiments, N can be between 2 and 8.

Figure 11C:
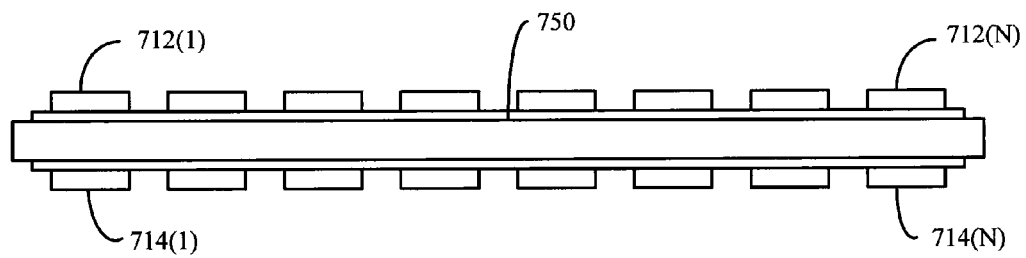
FIG. 11C is a cross-sectional view of the plug connector according to an embodiment of the present invention.

FIG. 11C illustrates a cross-sectional schematic view of contacts 712, 714 and positioning of the contacts. Contacts 712, 714 can be mounted on either side of a PCB 750. In some embodiments, contacts 712, 714 are part of a reversible or dual orientation unpolarized plug connector that can be mated with a corresponding receptacle connector in either of two orientations. In other embodiments, contacts 712, 714 are part of a polarized plug connector that can be mated with a corresponding receptacle connector in only a single orientation. Contacts 712, 714 can be made from a copper, nickel, brass, a metal alloy or any other appropriate conductive material. In some embodiments, spacing may be consistent between each of the contacts on the front and back sides and between the contacts and the edges of the connector providing 180 degree symmetry so that plug connector 700 can be inserted into and electrically mated with a corresponding receptacle connector in either of two orientations. When connector 700 is properly engaged with a receptacle connector, each of contacts $712_{(1)}$-$712_{(N)}$ and/or $714_{(1)}$-$714_{(N)}$ is in electrical connection with a corresponding contact of the receptacle connector.

Figure 11D:
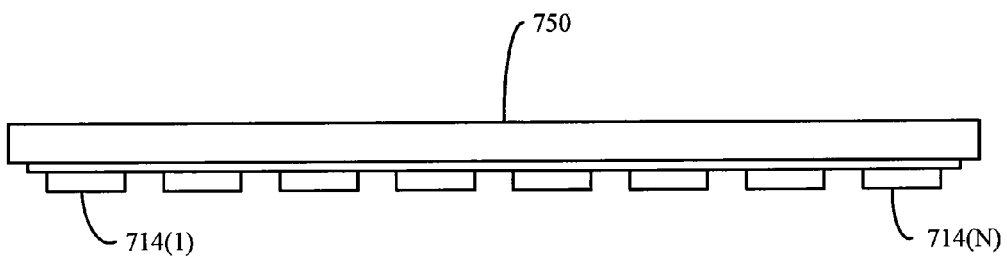
FIG. 11D is a cross-sectional schematic view of a single-sided plug connector according to an embodiment of the present invention.

It should be recognized that embodiments are not limited to a plug connector including contacts mounted on opposite sides. Rather, in some embodiments, contacts may be mounted on only one side of the plug connector. FIG. 11D illustrates an embodiment where contacts $714_{(1)}$-$714_{(N)}$ are mounted on only one side of PCB 150. In such a case, when connector 700 is properly engaged with a receptacle connector, each of contacts $714_{(1)}$-$714_{(N)}$ are in electrical connection with a corresponding contact of the receptacle connector.

Figure 11E:
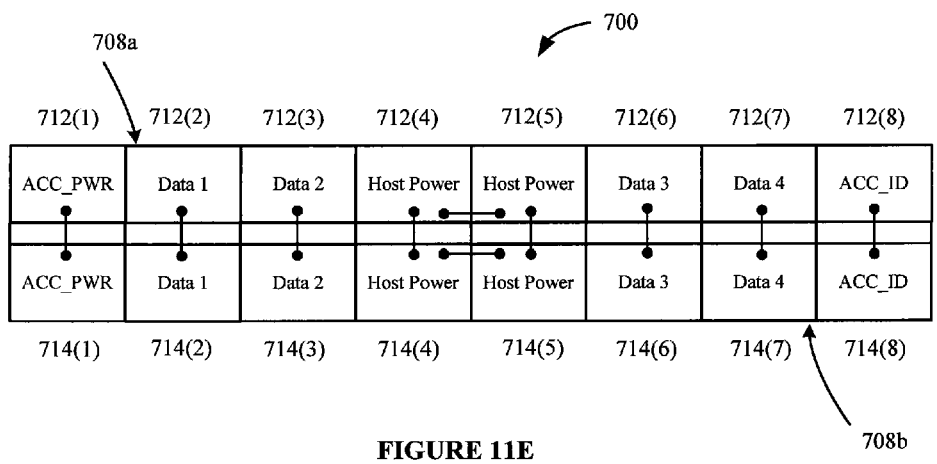
FIG. 11E is a pin-out of a plug connector according to an embodiment of the present invention.

FIG. 11E illustrates a pin-out configuration for connector 700 according to one particular embodiment of the present invention as described in connection with FIG. 11C above.

The pin-out shown in FIG. 11E includes four contacts 712(4), 712(5), 714(4), and 714(5) that are electrically coupled together to function as a single contact dedicated to carrying power to a connected host device. Connector 700 may also include accessory ID contacts 712(8) and 714(8); accessory power contacts 712(1) and 714(1); and eight data contacts arranged in four pairs. The four pairs of data contacts may be (a) 712(2) and 712(3), (b) 712(6) and 712(7), (c) 714(2) and 714(3), and (d) 714(6) and 714(7). Host power contacts 712(4), 112(5), 714(4), and 714(5) carry power from an accessory associated with connector 700 to a portable electronic device that is coupled to the accessory via connector 700. The host power contacts can be sized to handle any reasonable power requirement for an electronic device or host device, and for example, can be designed to carry between 3-20 Volts from an accessory to charge the portable electronic device connected to connector 700. In this embodiment, host power contacts 712(4), 712(5), 714(4), and 714(5) are positioned in the center of contact regions 708a, 708b to improve signal integrity by keeping power as far away as possible from the sides of ground ring 705.

Accessory power contacts 712(1) and 714(1) can be used for an accessory power signal that provides power from the electronic device (i.e. the host device) to an accessory. The accessory power signal is typically a lower voltage signal than the host power in signal received over host power contacts 712(4) and 712(5), for example, 3.3 volts as compared to 5 volts or higher. The accessory ID contacts provide a communication channel that enables the host device to authenticate the accessory and enable the accessory to communicate information to the host device about the accessory's capabilities as described in more detail below.

The four pairs of data contacts (a) 712(2) and 712(3), (b) 712(6) and 712(7), (c) 714(2) and 714(3), and (d) 714(6) and 714(7) may be used to enable communication between the host and accessory using one or more of several different communication protocols. For example, data contacts 712(2) and 712(3) are positioned adjacent to and on one side of the power contacts, while data contacts 712(6) and 712(7) are positioned adjacent to but on the other side of the power contacts. A similar arrangement of contacts can be seen for contacts 714 on the other surface of the PCB. The accessory power and accessory ID contacts are positioned at each end of the connector. The data contacts can be high speed data contacts that operate at a rate that is two or three orders of magnitude faster than any signals sent over the accessory ID contact which makes the accessory ID signal look essentially like a DC signal to the high speed data lines. Thus, positioning the data contacts between the power contacts and the ID contact improves signal integrity by sandwiching the data contacts between contacts designated for DC signals or essentially DC signals.

Figure 11F:
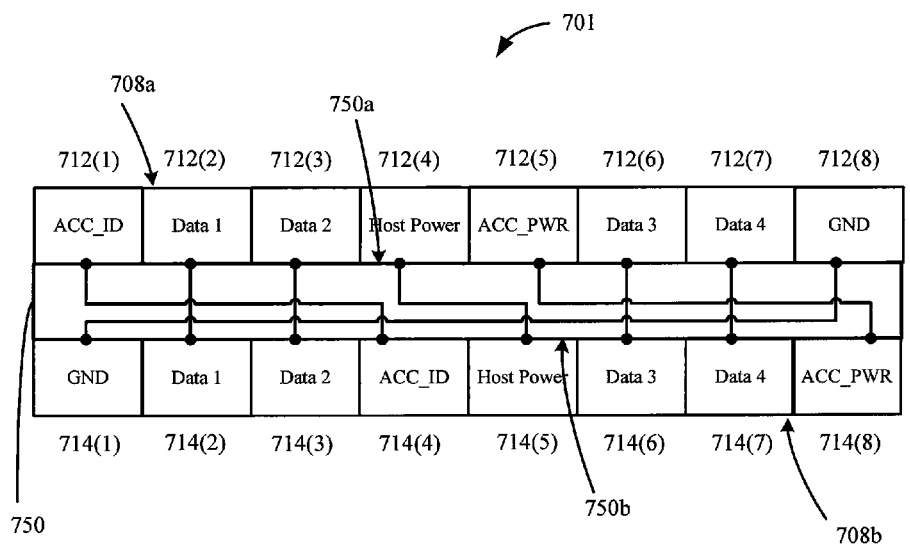
FIG. 11F is a pin-out of a plug connector according to another embodiment of the present invention.

FIG. 11F illustrates a pin-out configuration for a connector 701 according to another particular embodiment of the present invention.

Connector 701 is also a reversible connector just like connector 700. In other words, based on the orientation in which connector 701 is mated with a corresponding connector of a host device, either the contacts on the surface 708a or 708b are in physical and electrical contact with the contacts in the corresponding connector of the host device. As illustrated in FIG. 11F, connector 701 may have eight contacts arranged on an upper surface 750a of a PCB 750 and eight contacts arranged on a lower surface 750b of PCB 750.

Connector 701 includes two contacts 712(1) and 714(4) that can function as accessory ID contacts to carry the identification signals between the accessory and the portable electronic device. Contacts 712(1) and 714(4) are electrically connected to each other as illustrated in FIG. 11F. Connector 701 can have four pairs of data contacts, (a) 712(2) and 712(3), (b) 712(6) and 712(7), (c) 714(2) and 714(3), and (d) 714(6) and 714(7). In this particular embodiment, opposing data contacts, e.g., 712(2) and 714(2), are electrically connected to each other via PCB 750 as illustrated in FIG. 11E. Connector 701 may further include host power contacts 712(4) and/or 714(5) that may be electrically connected to each other. Host power contacts 712(4) and 714(5) can carry power to the host device that is mated with connector 701. For example, plug connector 701 may be part of a power supply system designed to provide power to the host device. In this instance, either contact 712(4) or 714(5) may carry power from the power supply to the host device, e.g., to charge a battery in the host device.

Connector 701 may further include accessory power contacts 712(5) and 714(8) that may be electrically connected to each other, e.g., via PCB 750. Accessory power contacts carry power from the host device to a connected accessory. For example, in some instances, an accessory connected to the host device may not be self-powered and may derive its power from the host device. In this instance, the host device can supply power to the accessory over either of the accessory contacts, depending on the orientation of connector 701 with respect to a corresponding connector of the host device. Connector 701 may further include two ground contacts 712(8) and 714(1) electrically connected to each other. The ground contacts provide a ground path for connector 701.

Figure 12A:
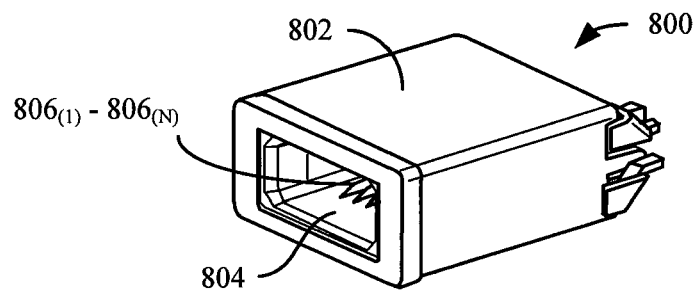
FIG. 12A illustrates a receptacle connector according to an embodiment of the present invention.

FIG. 12A illustrates a receptacle connector 800 according to an embodiment of the present invention. Receptacle connector 800 is an example of a receptacle connector used herein to explain various embodiments of the present invention. Receptacle connector 800 may correspond, for example, to connector 112 and/or connector 122 (FIG. 1), and in some embodiments is used to match plug connector 700. One skilled in the art will realize that many other forms and types of connectors other than receptacle connector 800 can be used.

Receptacle connector 800 includes a housing 802 that defines a cavity 804 and houses N contacts $806_{(1)}$-$806_{(N)}$ within the cavity. In operation, a connector plug, such as plug connector 700 (or connector 701) can be inserted into cavity 804 to electrically couple the contacts $712_{(1)}$-$712_{(N)}$ and/or $714_{(1)}$-$714_{(N)}$ to respective contacts $806_{(1)}$-$806_{(N)}$. Each of the receptacle contacts $806_{(1)}$-$806_{(N)}$ electrically connects its respective plug contact to circuitry associated with the electrical device in which receptacle connector 800 is housed. For example, receptacle connector 800 can be part of a portable media device (e.g., host device 110) and electronic circuitry associated with the media device is electrically connected to receptacle 800 by soldering tips of contacts $806_{(1)}$-$806_{(N)}$ that extend outside housing 802 to a multilayer board such as a printed circuit board (PCB) within the portable media device. Note that receptacle connector 800 is designed to be mated with a dual orientation, reversible plug connector and includes contacts on just a single side so the receptacle connector (and the electronic device the receptacle connector is part of) can be made thinner. In other embodiments, connector 800 may have contacts on each side while connector 700 may only have contacts on a single side or on both sides.

Figure 12B:
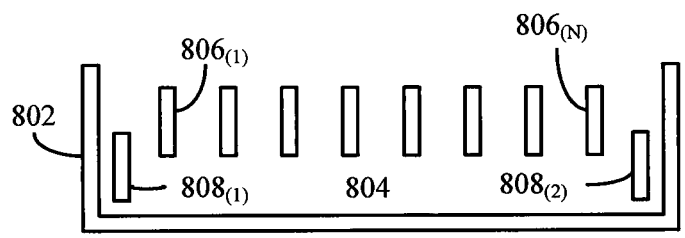
FIG. 12B is a cross-sectional view of the receptacle connector according to an embodiment of the present invention.

FIG. 12B illustrates a cross section view of receptacle connector 800 according to an embodiment of the present invention. As illustrated, in some embodiments, additional contacts $808_{(1)}$ and $808_{(2)}$ are located at either ends of contacts $806_{(1)}$-$806_{(N)}$. Contacts $808_{(1)}$ and $808_{(2)}$ may be used to detect whether the plug connector is fully inserted into cavity 804 or inserted to a point where contacts 712 (or 714) of plug connector 700 (or connector 701) are physically coupled to contacts 806 of receptacle connector 800. In some embodiments, contacts $808_{(1)}$ and $808_{(2)}$ can also be used to detect whether the plug connector has been disconnected from the receptacle connector. In some embodiments, contacts 808 can make contact with cap 720 of plug connector 700 when the plug connector is inserted beyond a certain distance within cavity 804. In some embodiments, contacts 808 are placed such that they will make contact with the ground ring of plug connector only when contacts 712 make a solid physical connection with contacts 806. In some embodiments, when contacts 808 connect to the ground ring of the plug connector, a signal may be generated indicating the connection.

Figure 12C:
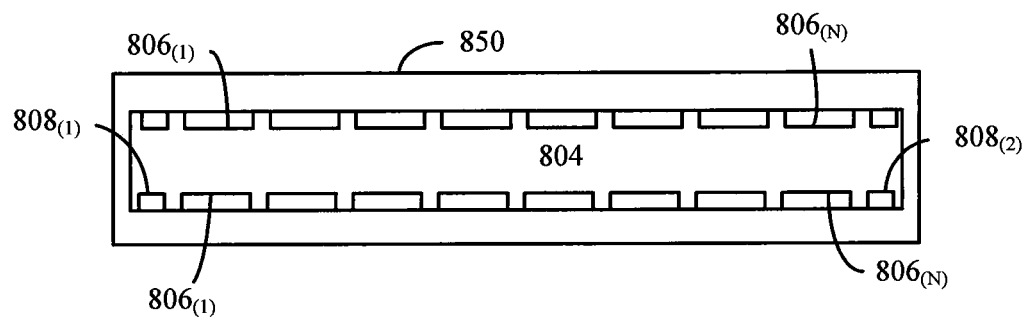
FIG. 12C illustrates a cross-sectional view of a receptacle connector having sixteen signal contacts and four connection detection contacts according to an embodiment of the present invention.

In some embodiments, receptacle connector 800 may have contacts both on the top side and the bottom side of cavity 804. FIG. 12C illustrates a cross-sectional view of a receptacle connector 850 that includes contacts $806_{(1)}$-$806_{(N)}$ on the top and contacts $806_{(1)}$-$806_{(N)}$ on the bottom. In some embodiments, a plug connector with electrically isolated contacts on the top and the bottom side may use the receptacle connector 850 of FIG. 14C.

Figures 12D, 12E, 12F:
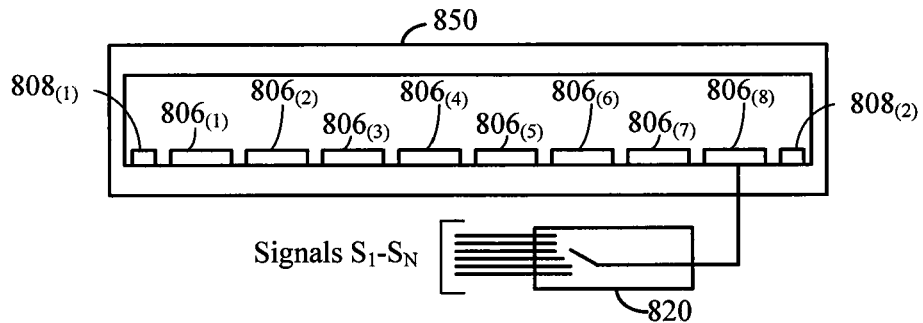
FIG. 12D is a cross-sectional view of a receptacle connector having eight signal contacts and two connection detection contacts according to an embodiment of the present invention.
FIGS. 12E and 12F are diagrams illustrating a pinout arrangement of a receptacle connector according to two different embodiments of the invention configured to mate with plug connectors 700 and 701, respectively, as shown in FIGS. 11E and 11F.

In some embodiments, receptacle connector 850 may have contacts $806_{(1)-(N)}$ only on a single side inside cavity 804 as described above. In a particular embodiment, receptacle connector may have eight (8) contacts $806_{(1)}$-$806_{(8)}$ as illustrated in FIG. 12D. Some or all of these contacts may be configured to perform one of several functions depending on the signals available on a plug connector. Plug connector 700 (or connector 701) may be associated with any one of several accessories (e.g., accessory 120) that may be designed to work with a host device (e.g., host device 110) that is associated with receptacle connector 850. For example, plug connector 700 (or connector 701) may be associated with an audio only accessory in which case the signals available on the contacts, e.g., $706_{(1)}$-$706_{(N)}$, of the plug connector may include audio and related signals. In other instances, where plug connector 700 (or connector 701) is associated with a more complex accessory such as video accessory, the contacts of plug connector may carry audio, video, and related signals. Thus, in order to enable receptacle connector 850 to be operable with various different types of signal, contacts $806_{(1)-(8)}$ of receptacle connector 850 can be made configurable based on the signals available from a plug connector 700 (or connector 701). In at least one embodiment, one or more contacts of plug connector 700 may be operable to send or receive power from a power source as already described herein, and one or more contacts of plug connector 700 may be operable to communicate information and/or various requests (and in some cases, simultaneously with power via the same pin) as already described herein. Similarly, one or more contacts of receptacle connector 800 may be operable to send or receive power from a power source as already described herein, and one or more contacts of receptacle connector 800 may be operable to communicate information and/or various requests (and in some cases, simultaneously with power via the same pin) as already described herein.

In the particular embodiment illustrated in FIG. 12D, receptacle connector 850 has eight contacts $806_{(1)-(8)}$ in addition to two connection detection contacts $808_{(1)}$ and $808_{(2)}$. The operation of the connection detection contacts $808_{(1)}$ and $808_{(2)}$ is described above in relation to FIG. 12B. Some or all of contacts $806_{(1)-(8)}$ have an associated switch that can configure the contact to carry one of many possible signals. However, for ease of explanation only one switch 820 coupled to contact $806_{(8)}$ is illustrated in FIG. 12D. It is to be noted that some or all of the other contacts $806_{(1)}$-$806_{(8)}$ may each have a similar switch 820 coupled to it. As illustrated in FIG. 12D, switch 820 can be used to configure contact $806_{(8)}$ to carry any one of signals $S_1$-$S_N$ depending on the configuration of the plug connector.

In a particular embodiment, contact $206_{(1)}$ may be an identification bus pins (ACC_1) and can be configured to communicate a command operable to cause an accessory to perform a function and provide a response to a host device unique to the command. The command may be any one or more of a variety of commands, including a request to identify a connector pin and select one of a plurality of communication protocols for communicating over the identified connector pin, a request to set a state of the accessory, and a request to get a state of the accessory. Contact $206_{(1)}$ may also or alternatively be configured to communicate power from the host device to the accessory (e.g., Acc_Pwr). For example, contact $206_{(1)}$ may be coupled to a positive (or negative) voltage source within the host device so as to generate a voltage differential with another pin (such as a ground pin which may be, e.g., contact $206_{(8)}$). In a particular embodiment, contact $806_{(1)}$ may correspond to data pin 114 and can be configured to carry one of (a) accessory identification signals, (b) accessory power, (c) host device identification signals, and (d) requests for identification signals. In other words, signals $S_1$-$S_N$ can any be selected from these signals for contact $806_{(1)}$ by its corresponding switch 820.

In a particular embodiment, contacts $806_{(2)}$ and $806_{(3)}$ may correspond to additional data pins 115 and can each be configured to carry one of a variety of signals, such as (a) USB differential data signals, (b) non-USB differential data signal, (c) UART transmit signal, (d) UART receive signal, (e) digital debug input/output signals, (f) a debug clock signal, (g) audio signals, (h) video signals, etc.

In a particular embodiment, contact $806_{(4)}$ may carry incoming power (e.g., a positive voltage relative to another contact such as a ground pin) to the host device (e.g., from a power source in or coupled to the accessory) with which receptacle connector 800 is associated. Contact $806_{(5)}$ may also function as an identification bus pin (ACC_ID) similar to contact $806_{(1)}$ described above. Contact $806_{(5)}$ may also or alternatively be configured to communicate power from the host device to the accessory (e.g., Acc_Pwr), depending on the orientation of a connected plug connector 700 (or connector 701) with respect to receptacle connector 800.

In a particular embodiment, contacts $806_{(6)}$ and $806_{(7)}$ may form a second pair of data pins (DP2/DN2) and can each be configured to carry one of (a) USB differential data signals, (b) Non-USB differential data signal, (c) UART transmit signal, (d) UART receive signal, (e) digital debug input/output signals, (f) a debug clock signal, (g) audio signals, (h) video signals, etc.

In a particular embodiment, contact $806_{(8)}$ may be a ground pin or otherwise provided at a voltage potential lower than contacts $806_{(1)}$, $806_{(4)}$, and $806_{(5)}$ so as to provide a voltage potential for power being provided to or from the host device.

In some embodiments, tab 704 has a 180 degree symmetrical, double orientation design which enables plug connector 700 (or connector 701) to be inserted into receptacle 800 in both a first orientation and a second orientation. Connector 700 (or connector 701) can be mated with connector 800 where contacts 712 of connector 700 can couple with contacts 806 of connector 800. We can refer to this as the first orientation for purposes of explanation. Details of several particular embodiments of connector 700 (or connector 701) are described in a commonly-owned U.S. patent application Ser. No. 13/607,366, titled "DUAL-ORIENTATION ELECTRONIC CONNECTOR", filed on Sep. 7, 2012 the contents of which are incorporated by reference herein in their entirety for all purposes.

In some embodiments, connector 700 (or connector 701) can be mated with connector 800 in a second orientation. In the second orientation, contacts 714 of connector 700 are coupled with contacts 806 of connector 800. The second orientation may be 180 degrees rotated from the first orientation. However, these are not the only possible orientations. For example, if connector 700 (or connector 701) is a square connector with a corresponding square connector 800, then connector 700 (or connector 701) can be mated with connector 800 in one of four possible orientations. Thus, one skilled in the art will realize that more than two orientations for the connectors may be possible.

FIGS. 12E and 12F illustrate pin-out configuration for a receptacle connector according to two different embodiments of the present invention. In one embodiment, receptacle connector 800 has a pin-out as shown in FIG. 12E that matches the pin-out of connector 700 in FIG. 11E and in another embodiment receptacle connector 800 has a pin-out as shown in FIG. 12F that matches pin-out of connector 701 of FIG. 11F. In each of FIGS. 12E and 12F, the ACC1 and ACC2 pins are configured to mate with either the accessory power (ACC_PWR) or accessory ID (ACC_ID) pins of the plug connector depending on the insertion orientation of plug connector, the pair of Data A contacts is configured to mate with either the pair of Data 1 contacts or the pair of Data 2 contacts of the plug connector, and the P_IN (power in) pin or pins are configured to mate with the Host Power contact or contacts of the plug connector. Additionally, in the pin-out of FIG. 12F, the GND contact is configured to mate with the GND contact in the plug connector.

Connectors 700 and 800 in certain embodiments are reversible connectors with exposed electrical contacts with a number of components. However, it will be appreciated by those of ordinary skill in the art that such connectors could operate equally well with fewer or a greater number of components than are illustrated in FIGS. 11A to 12F. Thus, the depiction of connectors 700 and 800 in FIGS. 11A to 12F should be taken as being illustrative in nature, and not limiting to the scope of the disclosure.

Various embodiments of systems, methods, and apparatus for determining the whether an accessory includes particular circuitry have been described. While these embodiments have been described in the context of FIGS. 1 to 12F, many modifications and variations are possible. The above description is therefore for illustrative purposes and is not intended to be limiting. Also, references to top or bottom, or front and back of the various structures described above are relative and are used interchangeably depending on the point of reference. Similarly, dimensions and sizes provided throughout the above description are for illustrative purposes only and the inventive concepts described herein can be applied to structures with different dimensions. Accordingly, the scope and breadth of the present invention should not be limited by the specific embodiments described above and should instead be determined by the following claims and their full extend of equivalents.

What is claimed is:

1. A method of determining whether an accessory includes particular circuitry, comprising:
    measuring, at a host device coupled to an accessory, a first voltage received from the accessory, the first voltage being received via a power pin provided in the host device;
    sending, by the host device, an instruction to the accessory to alter an impedance, at the accessory, of a power path between a power source and the host device;
    measuring, at the host device, a second voltage received from the accessory, the second voltage being received via the power pin provided in the host device; and
    determining, by the host device, whether the accessory includes particular circuitry based on the relationship between the first voltage and the second voltage.

2. The method of claim 1 wherein determining whether the accessory includes particular circuitry comprises:
    determining that the accessory includes the particular circuitry if the first voltage is greater than the second voltage by at least a predetermined amount; and
    determining that the accessory does not include the particular circuitry if the first voltage is not greater than the second voltage by at least the predetermined amount.

3. The method of claim 1 further comprising:
    if the accessory is determined to include the particular circuitry, coupling the power pin to power control circuitry of the host device operable to charge the host device using power provided by the power source.

4. The method of claim 1 wherein the instruction to the accessory includes one of:
    a first instruction instructing the accessory to operate in a state whereby a voltage passed through the accessory from the power source to the host device is substantially unaltered;
    a second instruction instructing the accessory to operate in a state whereby the voltage passed through the accessory from the power source to the host device is reduced to a first voltage when a first current is passed through the accessory; or
    a third instruction instructing the accessory to operate in a state whereby the voltage passed through the accessory from the power source to the host device is reduced by a second voltage when a second current is passed through the accessory.

5. A method of determining whether an accessory includes particular circuitry, comprising:
    measuring, at a host device coupled to an accessory, a first voltage received from the accessory, the first voltage being received via a power pin provided in the host device;
    sinking, at the host device, current from a power source via the accessory;
    measuring, at the host device, a second voltage received from the accessory, the second voltage being received via the power pin provided in the host device; and determining, by the host device, whether the accessory includes particular circuitry based on the relationship between the first voltage and the second voltage.

6. The method of claim 5 further comprising:
before measuring the second voltage, sending an instruction to the accessory to alter an impedance, at the accessory, of a power path between the power source and the host device.

7. The method of claim 5 further comprising:
before measuring the first voltage, disabling charging of the host device from power supplied by the power source via the appliance.

8. The method of claim 5 wherein the second voltage is measured after current is drawn from the power source via the accessory.

9. The method of claim 5 further comprising:
sending a request for an accessory identifier to the accessory to establish a connection with the accessory.

10. A host device comprising:
a power pin operable to receive a voltage from an accessory;
a data pin operable to communicate an instruction to the accessory; and
control circuitry operable to:
measure a first voltage received from the accessory via the power pin;
send an instruction to the accessory via the data pin, the instruction instructing the accessory to alter an impedance, at the accessory, of a power path between a power source and the host device;
sink current from the power source via the accessory;
measure a second voltage received from the accessory via the power pin; and
determine whether the accessory includes particular circuitry based on the relationship between the first voltage and the second voltage.

11. The host device of claim 10 wherein the control circuitry is further operable to charge the host device using power received at the power pin when it is determined that the accessory includes the particular circuitry.

12. The host device of claim 10 wherein the control circuitry is further operable to disable charging of the host device via the power path between the power source and the host device when it is determined that the accessory does not include the particular circuitry.

13. The host device of claim 10 wherein the control circuitry is further operable to:
measure the first voltage before sending the instruction to the accessory and before sinking current from the power source; and
measure the second voltage after sending the instruction to the accessory and after sinking current from the power source.

14. The host device of claim 10 further comprising:
power control circuitry including an overvoltage protection switch and processor; and
a charge control switch coupled between the power control circuitry and the power pin;
wherein the processor is operable to:
control the charge control switch to control charging of internal circuitry of the host device from the power source via the power pin, and
control the overvoltage protection switch to prevent the internal circuitry of the electronic from receiving power when a voltage at the power circuitry is greater than a predetermined voltage.

15. The host device of claim 10 wherein the control circuitry is further operable to:
send a request for an accessory identifier to the accessory on a first data pin of the host device;
determine whether a valid accessory identifier is received;
send another request for an accessory identifier to the accessory on a second data pin of the host device if it is determined that a valid accessory identifier is not received; and
receive power from the power source if it is determined that a valid accessory identifier is received.

16. The host device of claim 10 wherein the control circuitry is further operable to determine that the accessory includes the particular circuitry if the first voltage is greater than the second voltage by at least a predetermined amount, and to determine that the accessory does not include the particular circuitry if the first voltage is not greater than the second voltage by at least the predetermined amount.

17. The host device of claim 10 further comprising performing, by the host device, one or more operations based on whether or not the accessory includes particular circuitry.

18. The host device of claim 10 further comprising a connector that includes the power pin and the data pin.

19. The host device of claim 18 wherein the connector is a receptacle connector and the connector further includes first and second pairs of data contacts and wherein the host device further includes first switching circuitry operable to couple the first pair of data contacts to circuitry associated with one of a first plurality of communication protocols and second switching circuitry operable to couple the second pair of data contacts to circuitry associated with one of a second plurality of communication protocols.

20. The host device of claim 11 further comprising an internal battery, wherein being operable to charge the host device includes being operable to couple the power contact to the internal battery.

* * * * *